United States Patent
Na et al.

(10) Patent No.: US 7,763,287 B2
(45) Date of Patent: Jul. 27, 2010

(54) **EXTRACT OF *CERCIS CHINENSIS* HAVING ANTI-OXIDANT ACTIVITY AND ANTI-AGING ACTIVITY, AND COSMETICAL COMPOSITION CONTAINING THE EXTRACT FOR ANTI-OXIDATION, SKIN-AGING PROTECTION AND WRINKLE IMPROVEMENT**

(75) Inventors: Min Kyun Na, Daejeon-si (KR); Jae-Kuk Yoo, Daejeon-si (KR); Chan Bog Lee, Daejeon-si (KR); Jin Pyo Kim, Daejeon-si (KR); Gon Hyeok Lim, Daejeon-si (KR); Dong Il Min, Daejeon-si (KR); Young Min Jeon, Daejeon-si (KR)

(73) Assignees: Hankook Pharm. Co., Inc., Chungcheongnam-Do (KR); Hansaeng Cosmetic Co., Ltd., Daejeon-Si (KR)

( * ) Notice: Subject to any disclaimer, the term of this patent is extended or adjusted under 35 U.S.C. 154(b) by 2 days.

(21) Appl. No.: 12/032,453

(22) Filed: Feb. 15, 2008

(65) Prior Publication Data
US 2008/0187610 A1    Aug. 7, 2008

Related U.S. Application Data

(62) Division of application No. 10/537,688, filed as application No. PCT/KR03/02654 on Dec. 4, 2003, now abandoned.

(30) Foreign Application Priority Data
Dec. 27, 2002 (KR) .................. 10-2002-0085382
Nov. 28, 2003 (KR) .................. 10-2003-0085837

(51) Int. Cl.
*A01N 65/00* (2009.01)
(52) U.S. Cl. ........................................ 424/725
(58) Field of Classification Search ........................ None
See application file for complete search history.

(56) References Cited

U.S. PATENT DOCUMENTS

| 4,801,453 A | 1/1989 | Kosuge et al. |
| 2002/0110604 A1 | 8/2002 | Babish et al. |

FOREIGN PATENT DOCUMENTS

| CN | 1347705 | 10/2000 |
| CN | 1294926 | 5/2001 |
| DE | 20009867 | 8/2000 |
| JP | 61200922 | 9/1986 |
| JP | 07138175 | 5/1995 |
| JP | 8175960 | 7/1996 |
| JP | 8231953 | 9/1996 |
| JP | 10245075 | 9/1998 |
| KR | 2001096669 | * 11/2001 |

OTHER PUBLICATIONS

Lee et al., Kor. J. Pharmacogn., 30(4), 397-403, 1999.*
Kim et al., Yakhak Hoechi, 1995, 39(6), 600-9.*
Ma et al., Huaxue Yanjiu, 1997, 8 (4), 36-40.*
Na, MK, et al., "Antioxidant activity of *Cercis chinensis* and its protective . . . ", IFSCC Conference 2003, Sep. 22-24, Korea Proceeding Book 2 of 2, poster 42, 117-138, 29 REFS.
Halliwell, B., et al., "Oxygen Toxicity, Oxygen Radicals, Transition . . . ", Biochem. J., 219: 1-14, 1984.
Ames, B. N., et al., "Dietary Carcinogens and Anticarcinogens", Science, 221: 1256-1264, 1983.
Orr, W. C., "Extension of Life-Span by Overexpression . . . ", Science, 263: 1128-1130, 1994.
Sohal, R. S., "Simultaneous Overexpression of Copper . . . ", The Journal of Biological Chemistry, 270: 15671-15674, 1995.
Harley, C. B., "Telomeres Shorten during Ageing . . . ", Nature, 345: 458-460, 1990.
Ma, T., et al., "Extraction and Stability of the Red Pigment . . . ", Huaxue Yanjiu, 8: 36-40, 1997.
Li, S., et al., "Test on Extraction and Property for Red Pigment . . . ", Huaxue Shijie, 37: 416-418, 1996.
Kim, G. J., et al., "Phenolic Compounds from *Cercis chinensis* Leaves", Yakhak Hoechi, 39: 600-609, 1995.
Li, Y., et al., "A New Stilbene from *Cercis chinensis* Bunge", Ingenta Connect, 2 pages, 2007.

* cited by examiner

*Primary Examiner*—Michael V Meller
(74) *Attorney, Agent, or Firm*—Lucas & Mercanti, LLP

(57) ABSTRACT

The present invention relates to extract of *Cercis chinensis* having anti-oxidant activity and anti-aging activity containing compound of chemical formula 1 to chemical formula 20, and cosmetical composition for anti-oxidation, skin-aging protection and wrinkle improvement containing the extract as effective ingredient. The extract of present invention having protective effect on oxidative damage and skin damage, and inhibitory effect on age-dependent telomere shortening, so it can effectively used as skin-aging protection cosmetic.

9 Claims, 11 Drawing Sheets

EXTRACT OF *CERCIS CHINENSIS* HAVING ANTI-OXIDANT ACTIVITY AND ANTI-AGING ACTIVITY, AND COSMETICAL COMPOSITION CONTAINING THE EXTRACT FOR ANTI-OXIDATION, SKIN-AGING PROTECTION AND WRINKLE IMPROVEMENT

CROSS-REFERENCE TO RELATED APPLICATION

This patent application is a divisional application of U.S. patent application Ser. No. 10/537,688 filed Jun. 6, 2005 now abandoned, which in turn claims the benefit of priority from Korean Patent Application No. 10-2002-0085382 filed Dec. 27, 2002 and Korean Application No. 10-2003-0085837 filed Nov. 28, 2003 through PCT Application Serial No. PCT/KR2003/002654 filed Dec. 4, 2003, the contents of each of which are incorporated herein by reference.

FIELD OF THE INVENTION

The present invention relates to a plant extract having an anti-aging activity and a cosmetic composition containing the same as an effective ingredient. More particularly, the present invention relates to an extract of *Cercis chinensis* having an anti-oxidant activity and an anti-aging activity, and a cosmetic composition for anti-oxidation, skin-aging protection and wrinkle improvement containing the extract as an effective ingredient.

BACKGROUND

Aging means all the physiological changes of a body occurring by the lapse of time and the aging aspects and speed differ in each individual case and are affected by numbers of reasons. Even in an individual, aging shows different aspects in each organ, so that individual oriented study on aging has a limitation. More particularly, the functions of each organ and tissue are changed by aging, which is caused by the change of cell function. For example, the damage of nerve cells of brain causes the decrease of recognition, the damage of subcutaneous fat cells causes the loss of the elasticity of skin, the loss of melanin generating capability of melanocytes of hair root causes white hair, etc. So, the aging in an individual is caused by the aging of cells of the individual. Thus, recently, the study on aging has been focused on the cell-basis study. After all the efforts made by numbers of scientists to explain aging completely, the exact mechanism of aging has not been disclosed yet because of its various aspects and complexity. Just some theories on aging have been brought forward through phenomenological studies. Among them, an oxygen free radical theory and a telomere theory are given consequence. The former says that the accumulated oxidative stress resulted from oxygen free radicals generated during normal metabolism process is the major reason of aging and the latter says that a telomere located in the end of a chromosome gradually disappears after repeated cell division, resulting in the stop of cell division and cell death in the end. Other theories are also mutual assistant to give a full explanation on aging. More precisely, regarding an oxygen free radical theory, an oxygen free radical generated during normal metabolism process destroys cell components such as a lipid, a protein, a sugar or a DNA randomly, causing oxidative stress to a cell or a tissue, by which it causes not only in variety of diseases such as cancer, cardiovascular diseases such as cerebral apoplexy and arteriosclerosis, chronic inflammatory diseases such as rheumatism, respiratory diseases, autoimmune diseases, etc (Halliwell, B and Gutteridge, J. M. C, *Biochem. J.,* 1984, 219, 1-14; Freeman, B. A. and Grapo, J. D., *Lab Invest,* 1982, 47, 412-426; Ames, B. N., *Science,* 1983, 221, 1256-1264; Fridovich, I., *Arch. Biochem. Biophys.,* 1986, 247, 1-11; Vishwanath, M. S., *Nutrition in Clinical Practice,* 1995, 10, 19-25), but also aging to death by accumulating such oxidative damages for a long time. The oxygen free radical theory on aging was first proposed by Harman in 1956 (Harman, D., *Free radical theory of aging,* Alan R Liss, New York, 1936, 3-49), since then, numbers of experiments have given results supporting the theory. As an example, life span lengthened by controlling basal metabolic rate (BMR), that is, oxygen consumption, by restricting a diet or by restricting movement (Medvedev, Z. A., *Biol. Rev.,* 1990, 65, 375-398; Loe, J., Northrop, J. H., *J. Biol. Chem.,* 1971, 32, 103-121; Sohal, R. S., *Insect aging,* Springer-Verlag, Heidelberg, 1986, 23-44; Sohal, R. S., *Aging,* 1982, 5, 21-24).

In order to protect a living body from oxidative damages, the living body has anti-oxidant substances and anti-oxidant enzymes such as superoxide dismutase (SOD), catalase or peroxidase. But, their defensive power against oxygen free radicals becomes weaker, as getting old (Orr, W. C. and Sohal, R. S., *Science,* 1994, 263, 1128-1130; Sohal, R. S. et al., *J. Biol. Chem.,* 1995, 270, 15671-15674). For example, the activity of SOD separated from an old mouse was lower than that of a young mouse. Especially, life span of a fruit fly lengthened over 30% by increasing the activity of anti-oxidant enzymes, SOD and catalase, suggesting that oxygen free radical is closely connected with aging. Therefore, anti-oxidant agents that are able to remove oxygen free radical or to inhibit lipid peroxidation can be effectively used for the treatment of diseases caused by oxygen free radical and for the prevention of aging.

The lasting exposure on oxidative stress caused by harmful environment such as air pollution, UV, stress or diseases, increases radicals in a living body, creates wrinkles by destroying hyaluronic acid, elastin, collagen and a connective tissue of corium, and even causes diseases like dermatitis, pimples or skin cancer by destroying cells by oxidizing lipid in cell membrane. The radicals are related to the generation of melanin, being a reason of discoloration, freckles and wrinkles. As of today, ascorbic acid, alpha-tocopherol or SOD have been used for making skin protective cosmetics or medical supplies as a free radical eliminator. But, the price is high and the effect thereof is doubtful owing to the instability of the chemical mixture. Therefore, it is a common goal in the industries of medical supplies, food and cosmetics to develop a substance that is safe and has satisfactory effect of removing a free radical.

Telomere theory is the other major theory explaining aging. A normal cell of human goes through only determined numbers of cell division in vitro. That is, cell division is stopped after completing the scheduled division, which is called replicative aging. Telomere theory explains why such replicative aging is taking place (Kim, S. K., et al., *Oncogene* 21: 503-511 (2002); Harley, C. B., et al., *Nature* 345: 458-460 (1990); Olovnikov, A. M. *J. Theoret. Biol.* 41: 181-190 (1973); Harley, C. B., *Exp. Gerontol.* 27: 375-382 (1992); Allsopp, R. C., Weissman, I. L., *Oncogene,* 21: 3270-3273 (2002)). Telomere is a terminal part of linear chromosome of eukaryotes and has a very unique structure in which 'TTAGGG' sequence is repeated. Especially, guanine (G) forms a very stable G-quartet structure by hydrogen bond, so that it stabilizes and protects a chromosome (Moyzis, R. K., et al., *Proc. Natl. Acad. Sci.* 85: 6622-6626 (1988)). Telomeres in Human somatic cells, though, have been known to be shorten little by little every time cell division takes place (Harley, C. B., Futcher, A. B., Greider, C. W., *Nature* 345: 458-460 (1990); Harley, C. B. et al., *Exp. Gerontol.* 27: 375-382 (1992); Allsopp, R. C., Weissman, I. L., *Oncogene* 21: 3270-3273 (2002)). This is because of the "end replication problem", meaning that when DNA is replicated, the primer region of 3'-end is not replicated (Olovnikov, A. M. *J. Theoret. Biol.* 41: 181-190 (1973)). Thus, every time cell division takes place, a replicated DNA becomes shorter as much as the part of primer and so does a telomere in a chromosome. As the telomere continues to be shorter beyond critical point, single and double strands of DNA are cut off, resulting in that cell division is tied up in G1 stage by cyclin dependent kinase inhibitors (Harley, C. B., et al., *Exp. Gerontol,* 27: 375-382 (1992)). According to the recent study, the length of a telomere varies with oxidative stress. That is, oxidative stress accelerates the shortening of a telomere, which is because that the oxidative damage in the telomeric DNA part is less recovered than other parts of a chromosome (Saretzki, G., von Zglinicki, T., *Ann. New York Acad. Sci.* 959: 24-29 (2002); von Zglinicki, T., *Ann. New York Acad. Sci.* 908: 99-110 (2000); von Zglinicki, T., *TRENDS Biochem. Sci.* 27: 339-344 (2002); Lorenz, M., et al., *Free Radic. Biol. Med.* 31: 824-831 (2001)).

Based on those theories on aging, the present inventors have endeavored to find a novel substance from plants to inhibit skin aging. Plants have a well-established self-defense system to protect themselves from oxidative stress caused by lots of oxygen free radicals including superoxide radical, a residual product of photosynthesis. So, plants themselves are important sources for an anti-oxidant agent. Thus, the present inventors have investigated a radical scavenging activity and a lipid peroxidation inhibiting activity with 350 species of plants, and have selected a few candidates having an anti-oxidant activity. Considering easiness in securing resources and not being discovered about its components and activity, the present inventors have chosen *Cercis chinensis* as a final candidate for an anti-oxidant agent.

*Cercis chinensis*, a deciduous shrub, belongs to Leguminosae family and is native to China. It is 3-5 m tall and has no fluff on its twigs but has many lenticels. It has simple alternate leaves, which shape into a round heart, 6-11 cm in diameter, not fluffy and plain and smooth on the edge. The upper part of a leaf is dark green and glossy, but the back of the leaf is light green. Stipules are quadrangle and fall early. A flower is 1-2 cm long and a leaf axil has many blossoms. There is no rachis but a peduncle. A calyx has a bell shape and 5 blunt saw teeth on the upper edge. A corolla is butterfly-shaped and has magenta color. It has 5 irregular petals. It has 10 stamens that are all separated. The stamen base is attached in a calyx and a filament is thin and long. It has a single pistil. An ovary is glossy without a fluff. It has a hag, too. The upper style is bent and the stigma is small, short and plain. The flowering time is about April and leaves are out after blossom. As a legume, a fruit has a flat band shape whose end part shrinks to form a short bill. A pod is 7-12 cm long and ripens in August or September. A seed is round, flat and close to black (Lee, Y. N., Flora of Korea, Kyo-Hak Publishing Co., Ltd., Seoul, 1996, 362-363). The stem bark, root bark and stem of *C. chinensis* have been used to promote blood circulation, dysmenorrhea, edema, bruising and various injuries (Bae, K. H., The medicinal plants of Korea, Kyo-Hak Publishing, Seoul, Korea, 2000).

The present inventors have completed this invention by confirming that an extract of *Cercis chinensis*, unlike other synthesized anti-oxidant agents, is harmless to human, has an excellent cell protecting activity against oxidative stress and can even lengthen the life span of a cell by slowing the shortening speed of a telomere, so that it can be effectively used as a cosmetic composition for anti-aging, protection of skin elasticity and wrinkle care.

SUMMARY OF THE INVENTION

It is an object of this invention to provide an extract of *Cercis chinensis* having activities of anti-oxidation, anti-skin aging, protecting skin elasticity and preventing wrinkles, extracted by using water or alcohol as an extractant.

It is another object of this invention to provide a cosmetic composition for anti-oxidation, promotion of skin elasticity or wrinkle care which contains a chemical compound selected from a group consisting of the above extract or ingredients separated therefrom, presented in the chemical formula 1 to 20, as an effective ingredient.

It is an additional object of this invention to provide a pharmaceutical composition containing the above extract as an effective ingredient.

It is also an object of this invention to provide a preparation method of the above extract of the invention.

DETAILED DESCRIPTION OF PREFERRED EMBODIMENTS

In order to achieve the above object of the present invention, the present invention provides an extract of *Cercis chinensis* having activities of anti oxidation, anti-skin aging, protecting skin elasticity and preventing wrinkles, extracted by using water or alcohol as an extractant.

The present invention also provides a cosmetic composition for anti-oxidation, promotion of skin elasticity or wrinkle care which contains a chemical compound selected from a group consisting of the above extract or those separated therefrom, presented in the chemical formula 1 to 20, as an effective ingredient.

The present invention further provides a pharmaceutical composition containing the above extract as an effective ingredient.

The present invention also provides a preparation method of the above extract of the invention.

Hereinafter, the present invention is described in detail.

The present invention provides an extract of *Cercis chinensis* having activities of anti-oxidation, anti-skin aging, promoting skin elasticity or preventing wrinkles extracted by using water or alcohol as an extractant.

Based on the oxygen free-radical theory, the present inventors collected over 140 species of herb medicines and 210 species of plants to investigate an anti-oxidant activity, and then selected useful candidates. Among them, *Cercis chinensis* was selected as a final candidate because it was easy to secure resources and was not fully examined yet. And *Cercis chinensis* was finally confirmed, by the inventors, to have an anti-oxidant activity. *Cercis chinensis* used in the present invention was collected by Daeduk Science Town (Daejeon, Korea) and Chungnam National University (Daejeon, Korea) in September, 2001, and was identified by Prof. KiHwan Bae, College of Pharmacy, Chungnam National University. A voucher specimen (HK 1122) was deposited in the Jakwang Research Institute of the Hansaeng Cosmetics Co., Ltd.

In order to prepare an extract of *Cercis chinensis* of the present invention, alcohol aqueous solution was used as a solvent, which was preferably selected from a group consisting of methanol aqueous solution, ethanol aqueous solution, propanol aqueous solution and butanol aqueous solution.

Among them, ethanol aqueous solution was more preferable and particularly, 50-80% ethanol aqueous solution was preferable and 60% ethanol aqueous solution was more preferable.

In the present invention, an extract of *Cercis chinensis* was prepared by the steps of extracting alcohol crude extract of *Cercis chinensis*, more preferably, ethanol (EtOH) crude extract, by using ethyl acetate (EtOAC) and butanol (BuOH), obtaining each fraction from the above, separating ethyl acetate fraction and butanol fraction which have an antioxidant activity, and performing chromatography. At last, an extract including compounds represented in the chemical formula 1 to 20 was obtained from ethyl acetate fraction and butanol fraction (see FIG. 4 and FIG. 5). And the compound represented in chemical formula 15 (syringetin-3-O(2"-O-galloyl)-rutinoside), obtained in the present invention, was confirmed to be a novel compound.

<Chemical Formula 1>

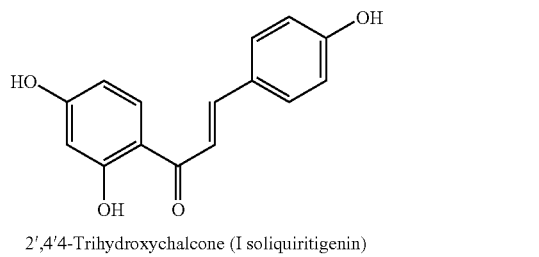

2',4'4-Trihydroxychalcone (I soliquiritigenin)

<Chemical Formula 2>

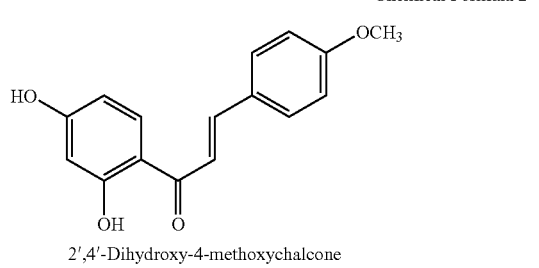

2',4'-Dihydroxy-4-methoxychalcone

<Chemical Formula 3>

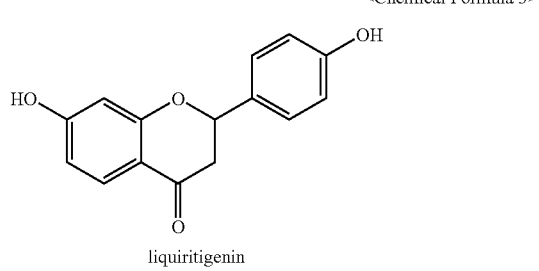

liquiritigenin

<Chemical Formula 4>

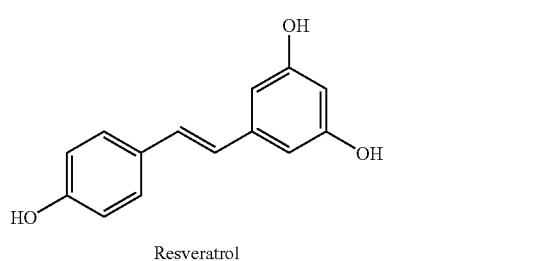

Resveratrol

-continued

<Chemical Formula 5>

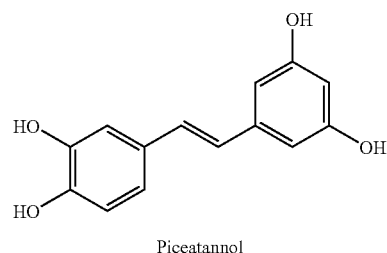

Piceatannol

<Chemical Formula 6>

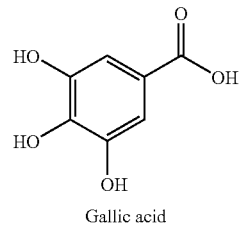

Gallic acid

<Chemical Formula 7>

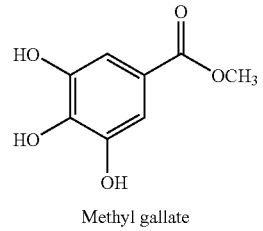

Methyl gallate

<Chemical Formula 8>

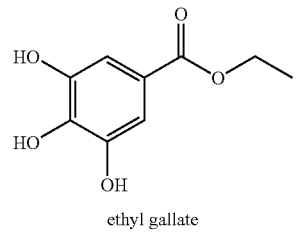

ethyl gallate

<Chemical Formula 9>

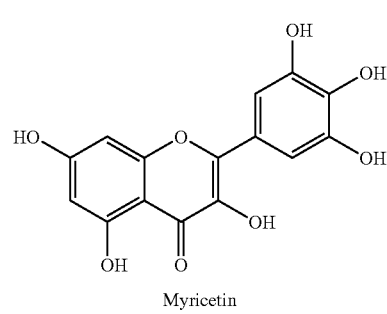

Myricetin

<Chemical Formula 10>
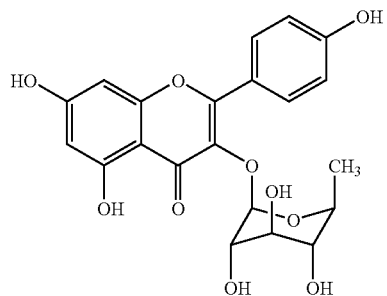
Afzelin
<Chemical Formula 11>
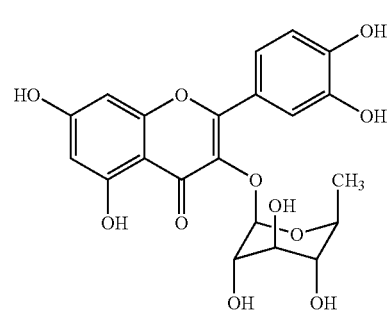
Quercetin-3-O-α-L-rhamnopyranoside (Quercitrin)
<Chemical Formula 12>
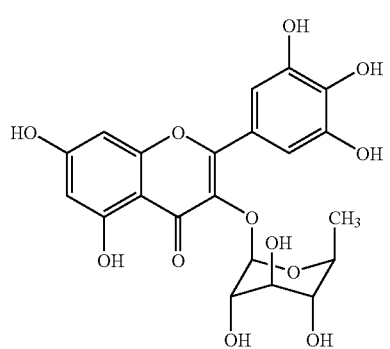
Myricetin-3-O-α-L-rhamnopyranoside
<Chemical Formula 13>
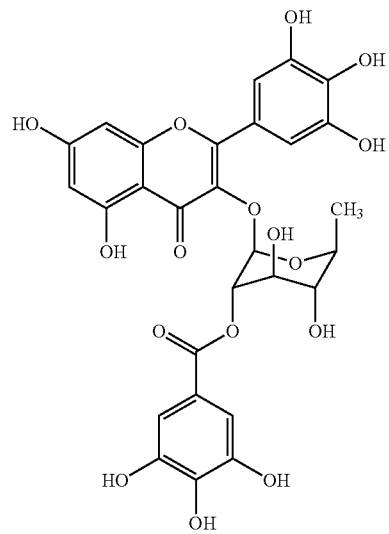
Myricetin-3-O-(2'-O-galloyl)-α-L-rhamnopyranoside
<Chemical Formula 14>
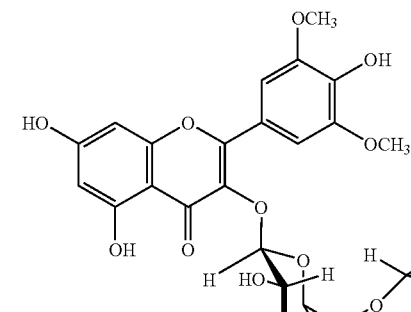
syringetin-3-O-rutinoside
<Chemical Formula 15>
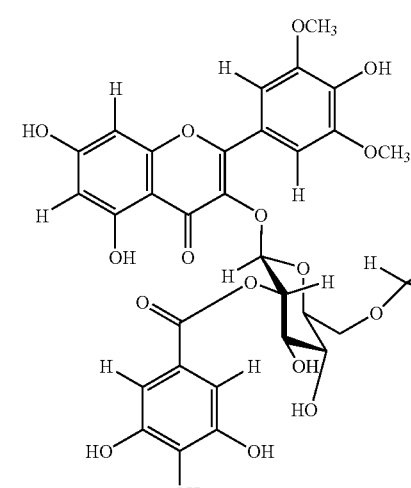
syringetin-3-O-(2''-O-galloyl)-rutinoside -continued <Chemical Formula 16>

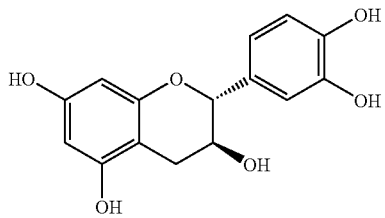

(+)-Catechin

<Chemical Formula 17>

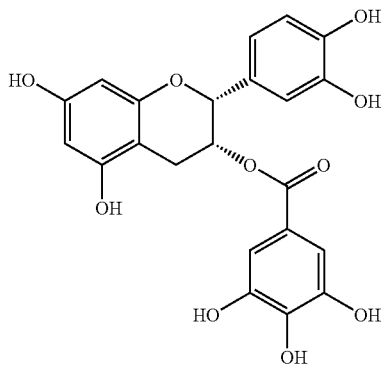

(-)-Epicatechin-3-O-gallate

<Chemical Formula 18>

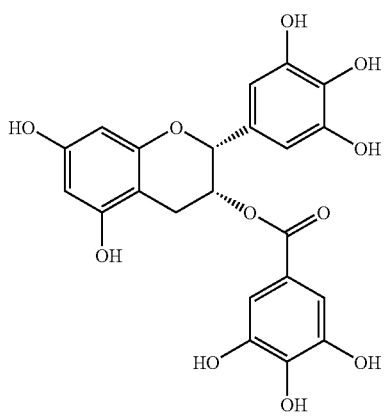

(-)-Epigallocatechin-3-O-gallate

<Chemical Formula 19>

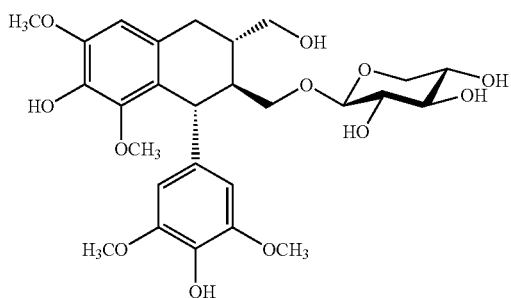

(-)-lyoniresinol 3a-O-β-D-xylopyranoside

-continued

<Chemical Formula 20>

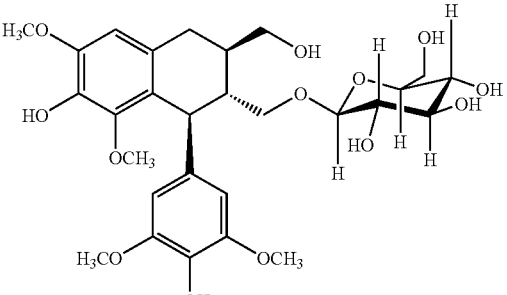

(+)-Lyoninesinol-3a-O-β-D-glucopyranoside

Of all the compounds represented in chemical formula 1 to 20, it is preferable for the extract of *Cercis chinensis* of the present invention to include the compound represented in chemical formula 6 by 0.01-1.00 weight %, the compound represented in chemical formula 12 by 0.01-1.00 weight % and the compound represented in chemical formula 5 by 0.01-0.5 weight % of the total weight of the extract.

The compounds of the invention represented in chemical formula 1-20 have anti-oxidant activities such as 1,1-Diphenyl-2-Pycryl-Hydrazyl radical scavenging activity (see Table 3), lipid peroxidation inhibitory activity (see Table 4), hydroxyl radical scavenging activity, nitric oxide scavenging activity (see Table 6) and superoxide radical scavenging activity (see Table 5).

Oxygen is essential for energy metabolism in aerobes, but once physical, chemical and biological stresses are given, oxygen changes into harmful active oxygen species such as superoxide anion radical, $H_2O_2$ and hydroxy radical, etc, causing a critical physiological disorders. Such active oxygen species attack an unsaturated fatty acid, one of the cell membrane components, leading to peroxidation. And the accumulated lipid peroxide might be the reason of various diseases including aging. In the present invention, an anti-oxidant activity of the extract of *Cercis chinensis* was measured by investigating active oxygen species scavenging activity and lipid peroxidation inhibitory activity of the extract. As a result, the anti-oxidant activity of the extract of *Cercis chinensis* was as much as or superior to that of vitamin E, a conventional anti-oxidant agent, or BHA (tert-butyl-4-hydroxyanisole), a synthesized anti-oxidant agent. Thus, the extract of *Cercis chinensis* of the invention was confirmed to have an excellent anti-oxidant activity.

The compounds of the present invention represented in chemical formula 1-20 also have such effects as cell protection (see Table 7) against oxidative damages caused by t-butylhydroperoxide(t-BuOOH), cell protection against UV irradiation (see FIGS. 6a and 6b), protection of a nude mouse against UV irradiation (see FIG. 7), inhibitory activity of lipid peroxidation induced by UV irradiation (see Table S), lengthen life span of a cell (see FIG. 8), and extension of the length of a telomere (see FIG. 9 and FIG. 10). Thus, it was confirmed that the extract of *Cercis chinensis* of the present invention and the active ingredients separated thereby have not only an excellent anti-oxidant activity but also a satisfactory cell aging inhibitory effect.

The present invention also provides a cosmetic composition for anti-oxidation, skin aging inhibition, promotion of skin elasticity or improvement of wrinkles containing a compound selected from a group consisting of the extract of

*Cercis chinensis* or compounds represented in chemical formula 1-20, separated from the extract above, as an effective ingredient.

An active ingredient separated from the extract of *Cercis chinensis* to be included in the cosmetic composition of the present invention is preferably selected from a group consisting of compounds represented in chemical formula 1 (isoliquiritigenin), chemical formula 2 (2',4'-dihydroxy-4-methoxychalcone), chemical formula 3 (liquiritigenin), chemical formula 4 (resveratrol), chemical formula 5 (piceatannol), chemical formula 6 (gallic acid), chemical formula 7 (methyl gallate), chemical formula 8 (ethyl gallate), chemical formula 9 (myricetin), chemical formula 10 (afzelin), chemical formula 11 (quercitrin), chemical formula 12 (myricitrin), chemical formula 13 (myricetin-3-O-(21'-O-galloyl)-α-L-rhamnopyranoside), chemical formula 14 (syringetin-3-O-rutinoside) chemical formula 15 (syringetin-3-O-2'-O-galloyl) rutinoside), chemical formula 16 ((+)-catechin) chemical formula 17 ((−)-epicatechin-3-O-gallate), chemical formula 18 ((−) epigallocatechin-3-O-gallate), chemical formula 19 ((−)-lyoniresinol 3a-O-β-D-xylopyranoside) and chemical formula 20 ((+)-lyoniresiol 3a-O-β-D-glucopyranoside).

The extract of *Cercis chinensis* or an active ingredient separated from the same has excellent anti-oxidant activities such as a peroxidation inhibitory activity and a radical scavenging activity, so that it can be effectively used as a cosmetic composition having the effects of skin aging inhibition, promotion of skin elasticity or wrinkle care owing to its capability of protecting skin and prolonging life span of a cell.

The cosmetic composition of the present invention can be used either as a raw material for a basic skin care cosmetics such as soft lotion, nutritive lotion, nutritive cream, essence, pack or bath powder, or as a external preparation for skin.

As a cosmetic composition is produced, the content of an oily component is determined after considering emulsification and economical efficiency. As an oily component, one or more selected from a group consisting of vegetable oil, mineral oil, silicon oil and synthetic oil can be used. Additionally, in order to enhance emulsification, surfactant and higher alcohol can be added by 0.1-5 weight %. An ordinary surfactant like nonionic surfactant is available and as for higher alcohol, an alcohol having 12-20 carbon number can be used singly or be mixed with another kind of alcohol.

For the production of a cosmetic composition, at least one of a thickener such as carbomer, xanthan gum, bentonite, etc, might be added to an aquatic component by 0.001-5 weight % to regulate a viscosity or a solidity.

For the production of a cosmetic composition of the present invention, it is also possible to add medicinal properties such as higher fatty acid, vitamin, etc, and other ordinary additives for a cosmetic such as UV protectors, anti oxidants, antiseptics, perfumery, coloring agents, pH regulators, etc.

In the preferred embodiment of the present invention, soft lotion, viscous solution, milky lotion, lotion and cream were produced by using an extract of *Cercis chinensis* of the present invention (see Table 9-Table 11).

In order to produce a cosmetic composition containing an extract of *Cercis chinensis*, the extract was added by 1-15 weight % in addition to the ordinary composition, and was more preferably added by 2-10 weight %.

The present invention further provides a pharmaceutical composition for anti-oxidation and anti-aging of skin, which contains an extract of *Cercis chinensis* of the present invention as an effective ingredient.

The pharmaceutical composition for anti-oxidation and anti-aging of skin, which contains an extract of *Cercis chinensis* of the present invention as an effective ingredient, is very useful for the treatment or the prevention of various diseases caused by oxidation of cell components by oxygen free radicals. The target diseases are cancer, aging, coronary heart disease, hyperlipemia, arteriosclerosis, multiple sclerosis, autoimmune encephalomyelitis, cerebral apoplexy, Alzheimer's disease and enteritis, but not always limited thereto.

The pharmaceutical composition containing an extract of *Cercis chinensis* can additionally include diluents, disintegrating agents, sweetening agents, lubricators, flavorings, etc, and can be produced in general forms of tablets, capsules, powders, granules, suspensions, emulsions, syrups, and other liquid forms.

Particularly, the pharmaceutical composition containing an extract of *Cercis chinensis* of the present invention as an effective ingredient can be produced in the forms of tablets, troches, lozenges, water-soluble or oily suspensions, powders or granules, emulsions, hard or soft capsules, syrups or elixirs, for oral administration. In order to make a form of tablets or capsules, binding agents such as lactose, saccharose, sorbitol, manitol, starch, amylopectin, cellulose or gelatin, diluents such as dicalcium phosphate, disintegrating agents such as cornstarch or sweet potato starch, lubricants such as magnesium stearic acid, calcium stearic acid, sodium stearylfumaric acid or polyethylenglycol wax, can be included. In order to make a formulation in the form of capsules, liquid carriers like fatty oil is included additionally to the above.

The pharmaceutical composition containing an extract of *Cercis chinensis* of the present invention can be administered parenterally. Intravenous injection, intramuscular injection or subcutaneous injection is the way of parenteral administration. In order to make a composition suitable for parenteral administration, an extract of *Cercis chinensis* of the present invention ought to be mixed with stabilizers or buffers in water to make a form of solutions or suspensions, which are finally formulated in the form of ampoules or vials.

The effective dosage of the composition of the present invention is determined by considering in vivo absorbance of an active ingredient, the rate of inactivation, excretory speed, age, sex and other conditions of a patient, the seriousness of a disease, etc. In general, in the case of oral administration, 2~200 mg of the extract of the present invention per 1 kg of weight, once a day or more, is recommended, and 10~100 mg is more preferable dosage The present invention also provides a preparation method of an extract of *Cercis chinensis*.

The preparation method of an extract of *Cercis chinensis* of the present invention is composed of the following steps:

1) Crude-extracting of pulverized powder of *Cercis chinensis* using alcohol;

2) Extracting the alcohol crude extract of the above step 1) with hexane, ethylacetate, and butanol in that order;

3) Performing methanol:water density gradient column chromatography with the ethylacetate fraction or butanol fraction obtained in the above step 2); and 4) obtaining a final anti-oxidant extract by performing column chromatography, TLC or HPLC with the fraction having an anti-oxidant activity obtained in the above step 3).

In the step 1), the alcohol is preferably one of methanol, ethanol, propanol or butanol, and among them, ethanol is more preferably selected. In that case, 60% ethanol is most preferable. In the preferred embodiment of the present invention, 60% ethanol crude extract was confirmed to have the highest activity by investigating DPPH radical scavenging activity of ethanol crude extract fractions of *Cercis chinensis* in the concentration ranging 0% to 100% (see FIG. 2).

BRIEF DESCRIPTION OF THE DRAWINGS

The application of the preferred embodiments of the present invention is best understood with reference to the accompanying drawings, wherein.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Extraction of an Effective Ingredient from *Cercis chinensis*

<1-1> Primary Separation of an Anti-Oxidant Active Fraction

Figure 1:
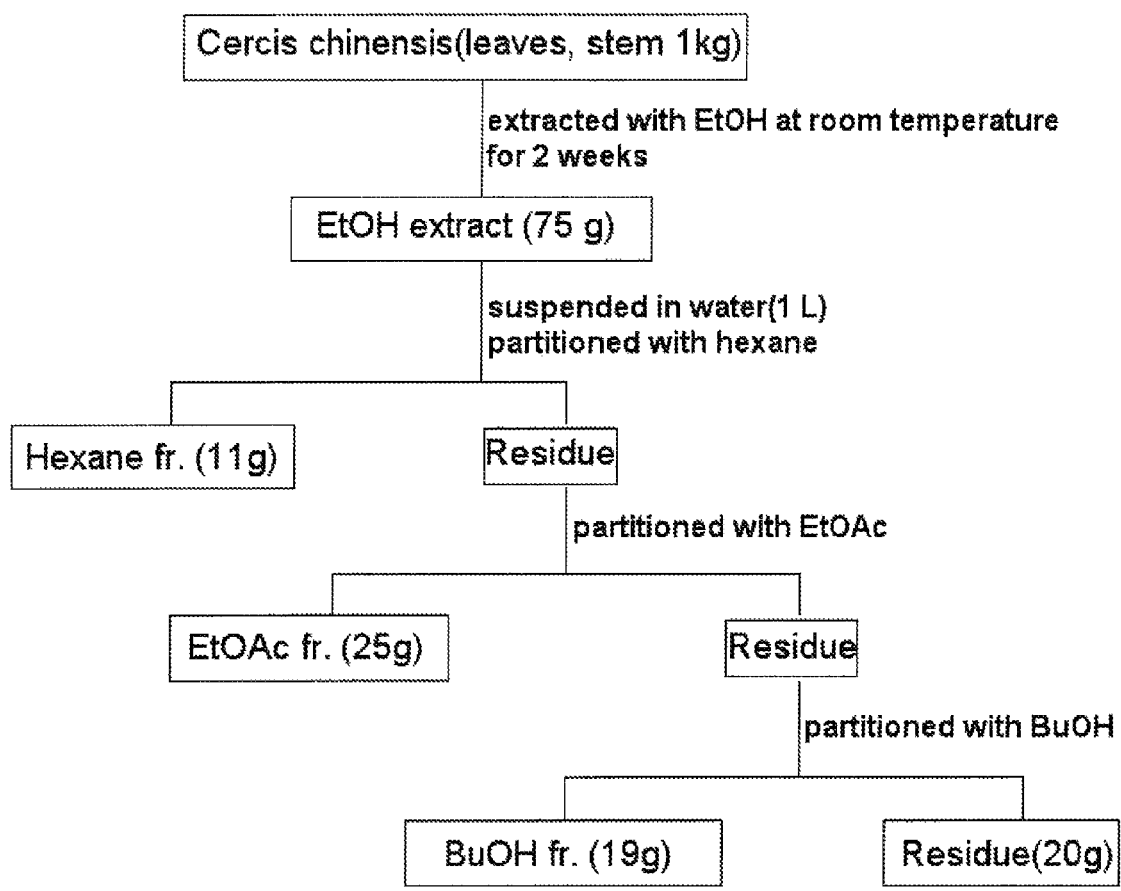
FIG. 1 is a schematic diagram showing the extracting procedure by hexane, ethylacetate, and butanol, in that order, after obtaining an ethanol crude extract from *Cercis chinensis*.

In order to extract an effective ingredient having an anti-oxidant activity from *Cercis chinensis*, an experiment was performed following the procedure represented in a schematic diagram of FIG. 1. Particularly, 1 kg of leaves and stems of *Cercis chinensis*, dried in shadow, were grinded to powder using a pulverizer, which was extracted by ethanol (EtOH) at room temperature twice at intervals of two weeks. For the extraction, ethanol solutions were prepared by adding ethanol gradually, 10% at a time, from 0% to 100%. The prepared ethanol solutions were used for the extraction. An anti-oxidant activity of the extract was investigated by a method using DPPH (1,1-diphenyl-2-pycryl-hydrazyl) (Taco, T. et al., *Biosci. Biotech. Biochem.*, 1994, 58, 1780-1783; Na, M. K. et al., *Nat. Prod. Sci.*, 2002, 8, 26-29). DPPH is a kind of stable free radical, and shows the maximum optical density at 517 nm as a radical. But, it looses absorbance when being scavenged. Based on that point, an anti-oxidant activity can be measured using DPPH. More particularly, each ethanol extract was obtained from *Cercis chinensis* according to different concentrations, which was diluted with DMSO(Sigma) to 3.125, 6.25, 12.25, 25 and 50 µg/ml respectively. Then, each solution was distributed into a 96 well plate by 10 µl each, into which 190 µl of DPPH(Sigma, St. Louis, Mo, USA) solution whose ethanol concentration was 2×10⁻⁴ M/ml was added. The plate was just left at room temperature for 30 minutes. Finally, $OD_{517}$ was measured at 517 nm. For a control, DMSO was added instead of the sample, and changes of optical density were investigated. DPPH radical scavenging activity was calculated by the below <Mathematical Formula 1>, and the concentration of sample that is able to scavenge DPPH by 50% was fixed as $IC_{50}$.

$$\text{DDPH Radical Scavenging Activity (\%)} = (A_{control} - A_{sample})/(A_{control}) \times 100 \quad \text{<Mathematica Formula 1>}$$

$A_{control}$: Optical density of control group (sample was not added), $A_{sample}$: Optical density of experimental group (sample was added).

Figure 2:
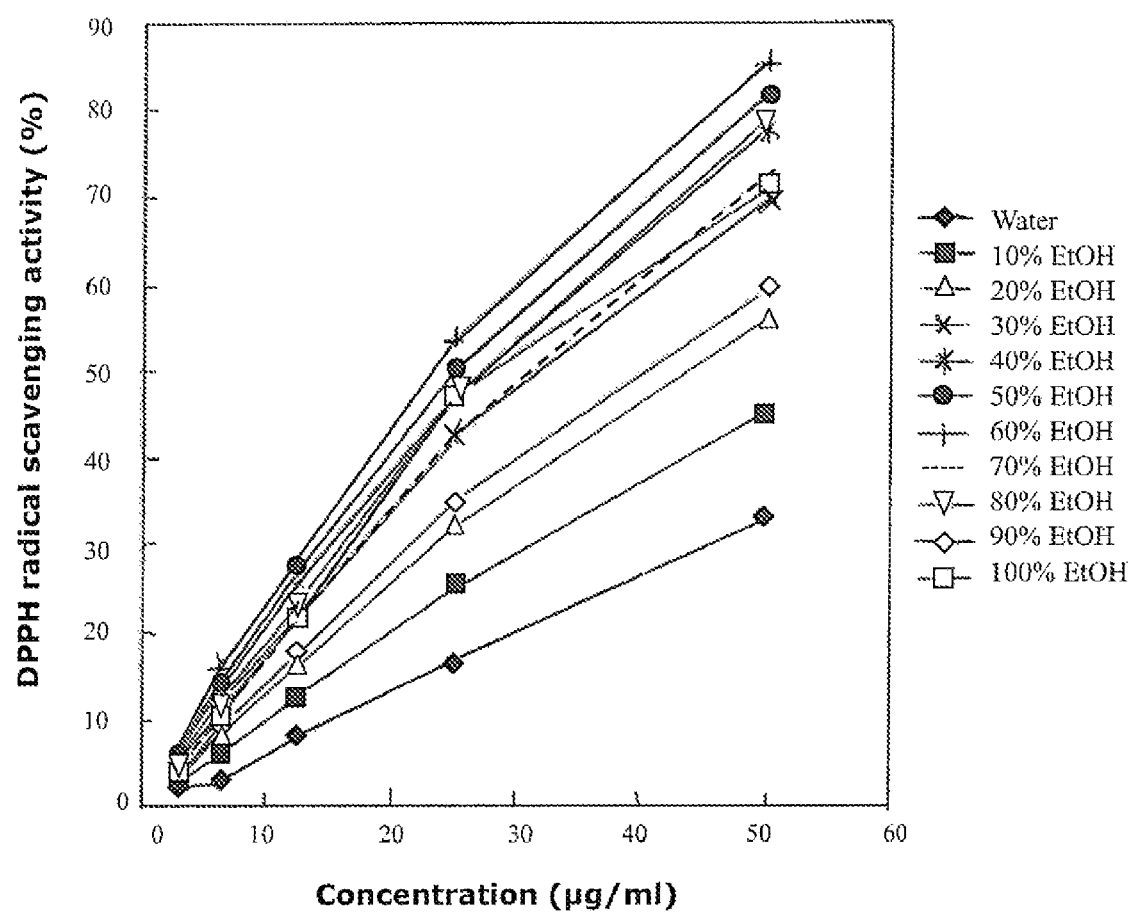
FIG. 2 is a graph showing DPPH radical scavenging activities of ethanol crude extracts in the ethanol concentration ranging 0% and 100% (10% difference for each crude extract), which were obtained from *Cercis chinensis*.

As a result, DPPH scavenging activity was increased dose dependently. While 0%, 10%, 20% and 90% ethanol extracts showed low radical scavenging activities, 30%, 40%, 50%, 60%, 70%, 80% and 100% ethanol extracts showed high radical scavenging activities as a whole. Especially, in the case of 60% ethanol extract, a radical scavenging activity became remarkably high as the concentration of the extract increased, and $IC_{50}$ was the lowest (26.6) among all the ethanol extracts, reflecting that the extract had the highest anti-oxidant activity (Table 1 and FIG. 2).

TABLE 1

| EtOH conc. | DPPH radical scavenging activity (%) | | | | | $IC_{50}$ (µg/ml) |
|---|---|---|---|---|---|---|
| | 3.125 µg/ml | 6.25 µg/ml | 12.5 µg/ml | 25 µg/ml | 50 µg/ml | |
| 0% | 2.4 | 2.9 | 8 | 16.8 | 33 | 75.2 |
| 10% | 2.9 | 6.1 | 12.6 | 25 | 45.3 | 54.3 |
| 20% | 3.7 | 8.4 | 16.3 | 32.2 | 56.1 | 43.3 |
| 30% | 5.4 | 12.3 | 22.4 | 42.4 | 69.7 | 33.8 |
| 40% | 6.5 | 13.2 | 25.9 | 47.4 | 77.9 | 29.8 |
| 50% | 6.7 | 14 | 27.1 | 50.1 | 81.9 | 28.2 |
| 60% | 7 | 15.6 | 28.5 | 53.6 | 85.3 | 26.6 |
| 70% | 3.5 | 10.9 | 21.9 | 42 | 72.8 | 33.0 |
| 80% | 4.2 | 11.4 | 23.1 | 46.9 | 78.9 | 30.2 |
| 80% | 3 | 8.9 | 17.6 | 35.3 | 59.5 | 40.4 |
| 100% | 4.1 | 10.7 | 21.7 | 47.4 | 70.7 | 32.7 |

After confirming that the 60% ethanol extract had the highest DPPH radical scavenging activity, each extract by different extractants was obtained. Particularly, the 60% ethanol extract was suspended in distilled water, which was extracted with hexane three times. By concentrating thereof under reduced pressure, 11 g of hexane fraction (referred as 'Fr' hereinafter) was obtained. The remaining suspension was extracted with ethyl acetate (EtOAc) three times. By concentration thereof under reduced pressure, 25 g of ethyl acetate fraction (referred as 'EtOAc Fr' hereinafter) was obtained. The remaining suspension was extracted again with water-saturated butanol (BuOH) three times. By concentration thereof under reduced pressure, 19 g of butanol fraction (referred as 'BuOH Fr' hereinafter) was obtained. And 20 g of remaining fraction was considered as a water fraction (FIG. 1).

In order to identify a fraction having an anti oxidant activity among hexane Fr, EtOAc Fr and BuOH Fr obtained above, a DPPH radical scavenging activity was measured using each extract of each fraction following the method used above. At this time, vitamin E, known to have high DPPH radical scavenging activity, was used as a comparing group.

Figure 3:
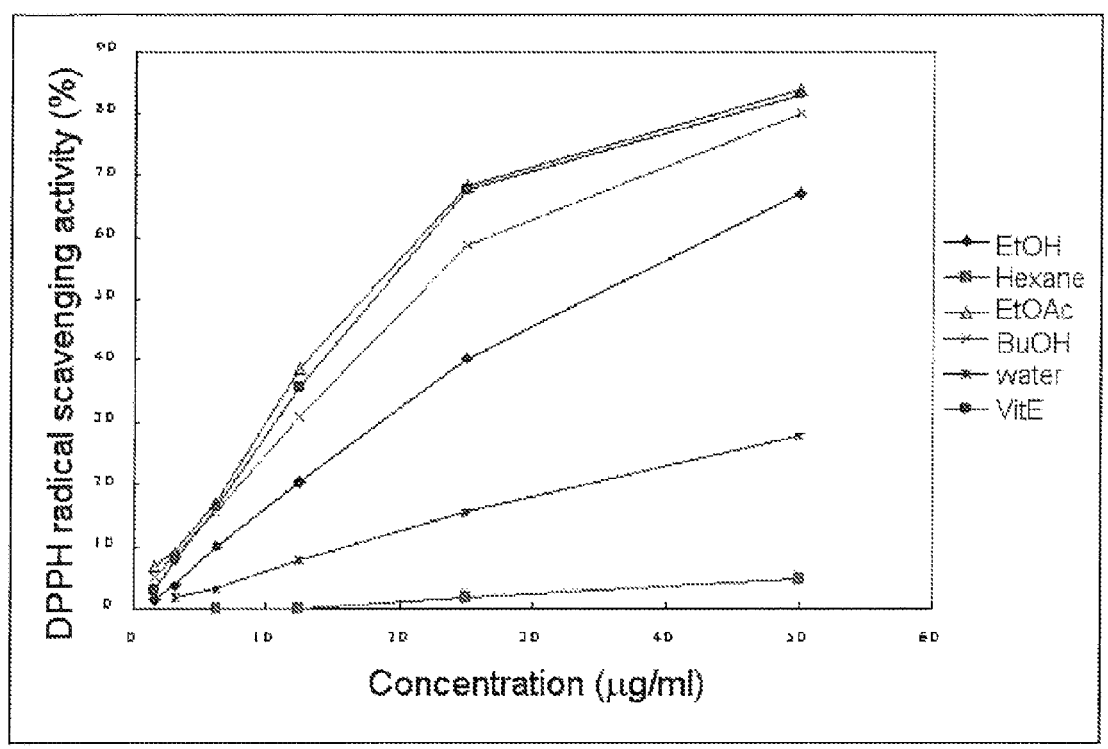
FIG. 3 is a graph showing a DPPH radical scavenging activity of each of hexane, ethylacetate, butanol and water fraction, and an ethanol extract.

As a result, $IC_{50}$s of EtOAc Fr and BuOH Fr were 24.0 and 27.0 μg/ml each, suggesting similar activities to that of vitamin E ($IC_{50}$: 24.9 μg/ml), a comparing group. But, other fractions showed weak activities (FIG. 3).

<1-2> Secondary Separation of an Anti-Oxidant Activity Fraction

Based on the result of the above Example <1-1>, column chromatography was performed with EtOAc Fr and BuOH Fr, both having a high activity. And, an anti-oxidant activity test was performed again with the obtained fractions to select one having a high anti-oxidant activity.

First, 11 sub-fractions (Fr.1~Fr.11) were obtained by YMC column chromatography (column size: 5×30 cm) with EtOAc Fr (25 g) using methanol:water (1:4→1:0) as a moving phase. YMC column chromatography (column size: 3×30 cm) was performed again with Fr.1 (3.6 g) among the above 11 sub-fractions, resulting in 5 sub-fractions (Fr.1-1~Fr.1-5). Fr.1-1 (450 mg) was selected for HPLC [column: μBondapak™$C_{18}$ (3.9×300 mm, Waters), moving phase: ACN:0.1% TCA (16:18), current speed: 1 ml/min., UV: 280 nm], from which 18 mg and 21 mg of compounds having retention times (referred as 'tr' hereinafter) of 11.1 minutes and 6.2 minutes respectively were obtained, and were named 'CCEA111' and 'CCEA112' respectively.

Second, collecting HPLC [YMC-Pack ODS-A column (20×250 mm), moving phase: methanol:water (3:7), current speed: 6 ml/min., UV: 254 nm] with Fr.1-2 (500 mg) was performed, resulting in 77 mg of a compound having 16 minute tR and 19 mg of a compound having 24 minute tR, which were named 'CCEA1211' and 'CCEA1212' respectively.

Third, collecting HPLC [YMC-Pack ODS-A column (20×250 mm), moving phase: ACN:0.1% TCA (25:75), current speed: 6 ml/min., detector: UV (280 nm)] with Fr.3 (4.8 g) was performed, resulting in 19 mg of a compound having 24.5 minute tR, which was named 'CCEA33'.

Next, Fr.4 (4.0 g) was divided into 6 sub fractions (Fr.4-1~Fr.4-6) by silica gel column chromatography (4×25 cm, 230-400 mesh, moving phase: chloroform:methanol (85:15)). Among them, Fr.4-1 (320 mg) was used for collecting HPLC [moving phase: methanol:water (35:65), current speed: 6 ml/min., UV: 254 nm], from which 30 mg of a compound having 25 minute tR was obtained and named 'CCEA413'. Likewise, Fr.4-4 (1 g) was also used for collecting HPLC [moving phase: methanol:water (1:1) current speed: 6 ml/min., UV: 254 nm], from which 57 mg of a compound having 15 minute tR was obtained and named 'CCEA442'.

Fr.6 (2.2 g) was divided into 3 sub-fractions (Fr.6-1~Fr.6-3) by silica gel column chromatography (3×30 cm, 230-400 mesh, moving phase: chloroform:methanol (10:1)). Among them, Fr.6-2 (200 mg) was used for collecting HPLC [moving phase: methanol:water (1:1), current speed: 6 ml/min., UV: 254 nm], from which 25 mg of a compound having 20 minute tR was obtained and named 'CCEA622'.

Next, silica gel chromatography (moving phase: chloroform:water (10:1) was performed with Fr.8 (2.1 g), from which 20 mg of a compound was obtained and named 'CCEA82'. After isolating the above CCEA82, the remaining fraction was dissolved in methanol. By recrystallizing thereof, 10 mg of a compound was obtained and named 'CCEA83'.

Figure 4:
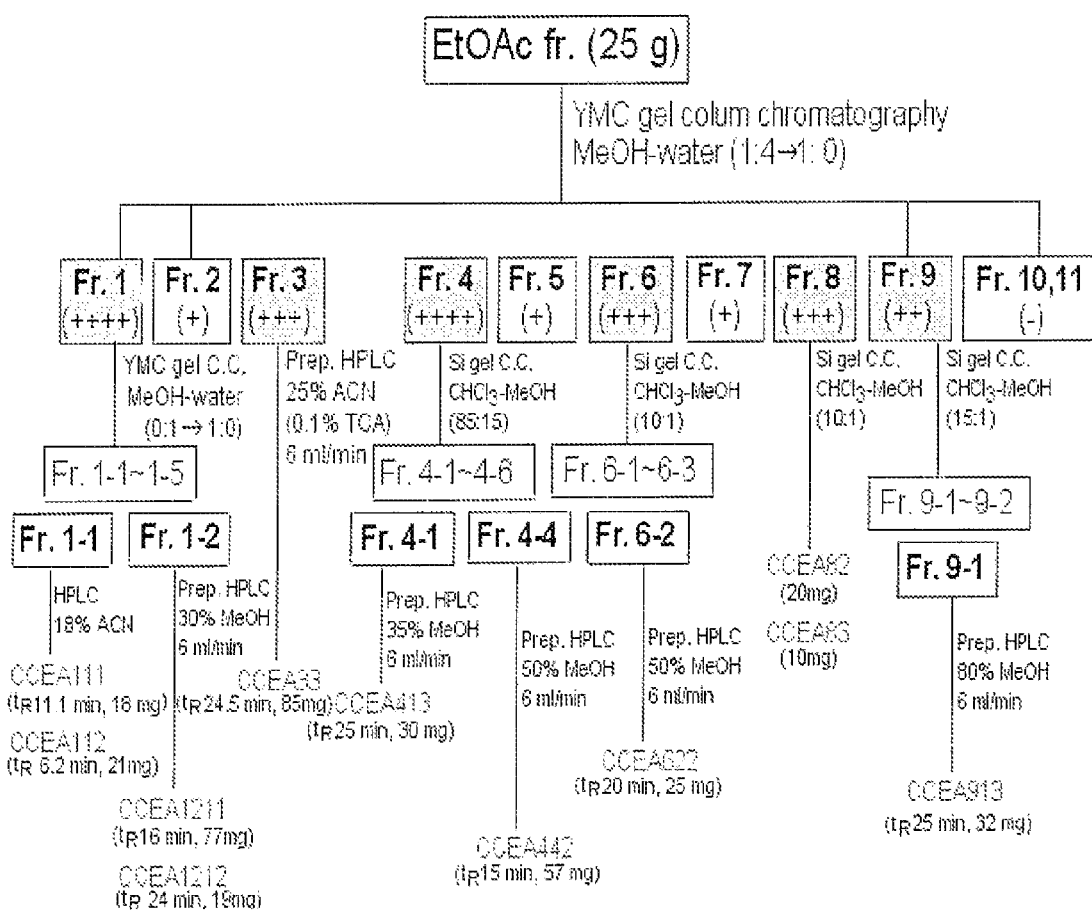
FIG. 4 is a schematic diagram showing a procedure of separating a compound having an anti-oxidant activity from an ethylacetate fraction.

Fr.9 (2.8 g) was divided into 2 sub-fractions (Fr.9-1~Fr.9-2) by silica gel column chromatography (moving phase: chloroform:methanol (15:1). Among them, Fr.9-1 (220 μg) was used for collecting HPLC [moving phase: methanol:water (4:1), current speed: 6 ml/min., UV: 254 nm], from which 32 μg of a compound having 25 minute tR, was obtained and named 'CCEA913' (FIG. 4).

YMC gel column chromatography (column size: 5×30 cm, moving phase: methanol:water (0:1→1:0)) was performed with BuOH Fr (19 g), resulting in 8 sub-fractions (Fr.1~Fr.8).

Silica gel column chromatography (moving phase: chloroform:methanol:water (70:30:5), column size: 3×30 cm, 230-400 mesh) was performed with Fr.2 (3.8 g), from which 5 sub-fractions (Fr.2-1~Fr.2-5) were obtained. Among those sub-fractions, Fr.2-3 (420 mg) was used for collecting HPLC [moving phase: acetonitrile:water (18:82), current speed: 6 ml/min., UV: 254 nm] to obtain Fr.2-3-1 and Fr.2-3-2. Fr.2-3-1 was used for collecting HPLC [moving phase: acetonitrile:water (10:90), current speed: 6 ml/min., UV: 254 nm] again, resulting in 32 mg of a compound having 15 minute tR that was named 'CCBt231'.

Silica gel column chromatography (3×30 cm, 230-400 mesh, moving phase: chloroform:methanol:water (70:30:5)) was also performed with Fr.5 (3 g), from which 4 sub-fractions (Fr.5-1~Fr.5-4) were obtained. Among them, Fr.5-2 (300 mg) was used for collecting HPLC [moving phase: methanol:water (35:65), current speed: 6 ml/min., UV: 254 nm], resulting in 20 mg of a compound having 25 minute tR and 13 mg of a compound having 30 minute tR. They were named 'CCBt521' and 'CCBt522'. YMC gel column chromatography (column size: 3×30 cm, moving phase: 30' methanol) was performed with Fr.5-3 (600 mg) to divide it into 4 sub-fractions (Fr.5-3-1~Fr.5-3-4). Among those sub-fractions, precipitation from Fr.5-3-3 was purified to obtain 29 mg of a compound that was named 'CCBt533'.

YMC column chromatography (column size: 3×30 cm) was performed again with Fr.6 (3.2 g) to divide it into 4 sub-fractions (Fr.6-1~Fr.6-4). Among them, Fr.6-2 (370 mg) was used for collecting HPLC [moving phase: methanol:water (3:7), current speed: 61 ml/min., UV: 254 nm], resulting in a compound (9 mg) having 26 minute tR and a compound (16 mg) having 28 minute tR. They were named 'CCBt622' and 'CCBt623'. Fr.6-4 (200 mg) was also used for collecting HPLC (moving phase: methanol:water (4:6), current speed: 6 ml/min.), resulting in a compound (5 mg) having 18 minute tR, which was named 'CCBt641'.

Figure 5:
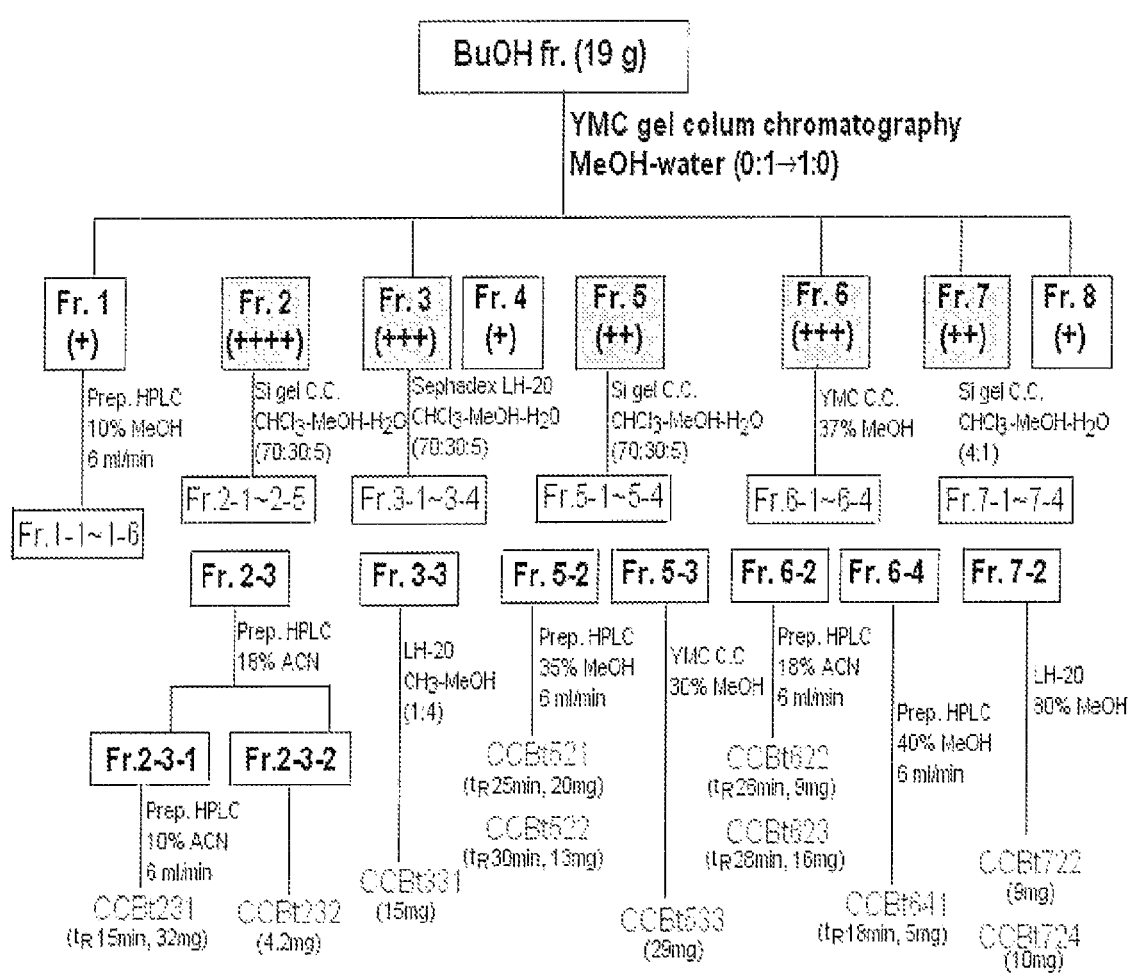
FIG. 5 is a schematic diagram showing a procedure of separating a compound having an anti-oxidant activity from a butanol fraction

Silica gel column chromatography (moving phase: chloroform:methanol, column size: 3×30 cm) was performed with Fr.7 (1.9 g), resulting in 4 sub-fractions (Fr.7-1~Fr.7-4) Fr.7-2 (50 mg) was used for Sepadex LH-20 column chromatography (moving phase: 80% methanol, column size: 3×30 cm) to divide it into 5 sub-fractions (Fr.7-2-1~Fr.7-2-5). Among them, Fr.7-2-2 was dissolved in methanol to recrystallize again, from which a compound (9 mg) was obtained and named 'CCBt722'. Besides, another compound (10 mg) was obtained by purifying the precipitation extracted from Fr.7-2-4, which was named 'CCBt724' (FIG. 5).

<1-3> Analysis of the Structures of the Separated Compounds

The structures of 21 fractions separated in the above Example <1-2> were examined. Particularly, melting point was investigated by an electrothermal melting point apparatus (Electrothermal Eng. Ltd., AZ 9003), degree of rotation was examined by using a DIP-370 digital polarimeter (JASCO), IR spectrum was investigated by using a IR report-100 spectrophotometer (JASCO), mass-analysis was performed with a tandem mass spectrometer (Jeol, JMS HX-110/110A), NMR assay was performed with a NMR spectrophotometer (Bruker, NMR AMX-600 spectrometer), and gas chromatography was performed by using a STAR 3400CX GC (Varian) according to the manufacturer's instruction. Considering all the results of the above tests (melting point, degree of rotation, IR spectrum, mass, and NMR), a structure of a compound was determined.

As a result, compounds were classified by a structure into chalcones, stilbenes, phenolics, flavonols, flavanols and lignans as seen in the below Table 2. Each was confirmed to be a compound represented in <Chemical Formula 1>-<Chemical Formula 20>. Especially, a compound (syringetin-3-O-(2"-O-galloyl)-rutinoside) represented in <Chemical Formula 15> had characteristics explained hereinafter, by which the compound was determined to be a novel compound.

<Characteristics of Chemical Formula 15>

Light-yellow powder, $FeCl_3$, Mg—HCl, Zn—HCl test: positive,

Positive FAB-MS: m/z 823$[M+H]^+$ $[\alpha]_D$-80 (c 0.1, MeOH)

IR $V_{max}$ $cm^{-1}$: 3400 (—OH), 1650 (C=O), 1610, 1500, 1455 (aromatic C=C), 1200, 1020 (glycosidic C—O)

UV $\lambda_{max}$ nm (log $\epsilon$): 257 (3.60), 360 (3.82)

$^1$H-NMR (600 MHz, DMSO-d6): 7.46 (2H, s, H-2, 6), 6.91 (2H, s, galloyl-2, 6), 6.48 (1H, d, J=1.8 Hz, H-8), 6.21 (1H, d, J=1.8 Hz, H-6), 5.48 (1H, d, J=7.2 Hz, glc-1), 4.49 (1H, s, rham-1), 3.84 (6H, s, OMe-3, 5), 3.70 (1H, d, J=10.2 Hz, glc-6), 3.38 (1H, d, J=10.2 Hz, glc-6), 1.00 (3H, d, J=5.0 Hz, rham-6)

$^{13}$C-NMR (150 MHz, DMSO-d6): 156.3 (C-2), 133.1 (C-3), 177.3 (C-4), 161.1 (C-5), 98.6 (C-6), 164.0 (C-7), 93.9 (C-8), 156.4 (C-9), 104.0 (C-10), 119.7 (C-1), 106.9 (C-2, 6), 147.4 (C-3, 5), 138.6 (C-4), 100.8 (glc-1), 76.4 (glc-2), 74.9 (glc-3), 70.1 (glc-4), 74.3 (glc-5), 66.7 (glc-6), 101.0 (rha-1), 70.2 (rha-2), 70.5 (rha-3), 71.7 (rha-4), 68.3 (rha-5), 17.6 (rha-6), 165.3 (C=O), 120.4 (galloyl-1), 108.7 (galloyl-2, 6), 145.3 (galloyl-3, 5), 137.9 (galloyl-4).

TABLE 2

| Classification | Fraction | Compound |
|---|---|---|
| Chalcones | CCEA82 | Chemical Formula 1 (isoliquiritigenin) |
| | CCEA83 | Chemical Formula 2 (luquiritigenin) |
| | CCEA913 | Chemical Formula 3 (2',4'-dihydroxy-4-methoxychalcone) |
| Stilbenes | CCEA622 | Chemical Formula 4 (piceatannol) |
| | CCEA442 | Chemical Formula 5 (resveratrol) |
| Phenolics | CCBt231 | Chemical Formula 6 (gallic acid) |

TABLE 2-continued

| Classification | Fraction | Compound |
|---|---|---|
| | CCEA1212 | Chemical Formula 7 (methyl gallate) |
| | CCEA33 | Chemical Formula 8 (ethyl gallate) |
| Flavonols | CCEA413 | Chemical Formula 9 (myricetin) |
| | CCBt722 | Chemical Formula 10 (afzelin) |
| | CCBt623 | Chemical Formula 11 (quercitrin) |
| | CCBt622 | Chemical Formula 12 (myricitrin) |
| | CCBt641 | Chemical Formula 13 (myricetin-3-O-(2"-O-galloyl)-α-L-rhamnopyranoside) |
| | CCBt533 | Chemical Formula 14 (syringetin-3-O-rutinoside) |
| | CCBt724 | Chemical Formula 15 (syringetin-3-O-(2"-O-gallate) |
| Flavanols | CCEA1211 | Chemical Formula 16 ((+)-cathechin) |
| | CCEA111 | Chemical Formula 17 ((−)-epicatechin-3-O-gallate) |
| | CCEA112 | Chemical Formula 18 ((−)-epigallocatechin-3-O-gallate) |
| Lignans | CCBt521 | Chemical Formula 19 ((−)-lyoniresiol 3a-O-β-D-xylopyranoside) |
| | CCBt522 | Chemical Formula 20 ((+)-lyoniresiol 3a-O-β-D-glucopyranoside) |

Example 2

Measurement of DPPH Radical Scavenging Activity

In order to investigate anti-oxidant activities of the extracts containing the compounds represented by <Chemical Formula 1>-<Chemical Formula 20>, which were separated in the above Example 1, DPPH radical scavenging activities of them were measured by the same method as used in the above Example 1. At this time, BHA (tert-butyl-4 hydroxyanisole) and α-tocopherol, synthetic anti-oxidant agents, were used as positive controls.

As a result, phenolic acids and flavonoid compounds showed strong radical scavenging activities, dose dependently. And stilbene compounds showed comparatively strong radical scavenging activities. In particular, galloyl esters including gallic acid had strong activities. For example, $IC_{50}$ values of compounds represented by <Chemical Formula 6> (gallic acid), <Chemical Formula 7> (methyl gallate), <Chemical Formula 8> (ethyl gallate), <Chemical Formula 17> ((−)-epicatechin-3-O-gallate), <Chemical Formula 18> ((−)-epigallocatechin-3-O-gallate) and <Chemical Formula 13> (myricetin-3-O-(2-O-galloyl)-a-L-rhamnopyranoside) were 5.1±0.4, 5.3±0.3, 7.0±1.1, 6.8±0.5, 6.7±0.4 and 8.6±0.7 g/ml, respectively, suggesting that there was no big difference among those compounds in the activity, and all of them showed remarkably stronger radical scavenging activities than α-tocopherol ($IC_{50}$ 25.4±0.9 g/ml) and BRA ($IC_{50}$ 15.3±0.6 g/ml), both used for positive controls (Table 3).

If an electron donating group is replaced on ortho-position of benzene ring, phenoxy radical becomes stable easily, resulting in the increase of a radical scavenging activity (Cu-velier, M. E., Richard, H., Berset, C., *Biosci. Biotechnol. Biochem.* 56: 324-325 (1992); Kikuzaki, H., et al., *J. Agric. Food Chem.* 50: 2161-2168 (2002)). Galloyl group shows a strong radical scavenging activity because it is replaced on the location near 3 hydroxyl groups, which effectively makes phenoxy radical stable. As shown in Table 3, in addition to Galloyl group, flavonoid compounds represented by <Chemical Formula 16> ((+)-catechin), <Chemical Formula 9> (myricetin), <Chemical Formula 10> (afzelin), <Chemical Formula 11> (quercitrin) and <Chemical Formula 12> (myricitrin) were also confirmed to have a strong radical scavenging activity, which seemed to be because they had phenolic substituents making phenoxy radical stable in flavonoid structure. In conclusion, a compound containing a substituent having a great electron donating capability can increase a radical scavenging activity, which was in accordance with the report by Pekkarinene, et al. (Pekkarinen, S. S., et al., *J. Agric. Food Chem.* 47: 3036-3043 (1999)).

TABLE 3

| Classification | Compound | DPPH radical scavenging activity IC$_{50}$ (µg/ml) |
|---|---|---|
| Chalcones | Chemical Formula 1 | >50 |
| | Chemical Formula 2 | >50 |
| | Chemical Formula 3 | >50 |
| Stilbenes | Chemical Formula 4 | 20.9 ± 1.3 |
| | Chemical Formula 5 | 39.5 ± 2.8 |
| Phenolics | Chemical Formula 6 | 5.1 ± 0.4 |
| | Chemical Formula 7 | 5.3 ± 0.3 |
| | Chemical Formula 8 | 7.0 ± 1.0 |
| Flavonols | Chemical Formula 9 | 7.3 ± 0.3 |
| | Chemical Formula 10 | 33.4 ± 1.6 |
| | Chemical Formula 11 | 12.4 ± 0.6 |
| | Chemical Formula 12 | 11.6 ± 0.4 |
| | Chemical Formula 13 | 8.6 ± 0.7 |
| | Chemical Formula 14 | 35.1 ± 1.5 |
| | Chemical Formula 15 | 29.2 ± 1.8 |
| Flavonols | Chemical Formula 16 | 15.6 ± 0.8 |
| | Chemical Formula 17 | 6.8 ± 0.5 |
| | Chemical Formula 18 | 6.7 ± 0.4 |
| Lignans | Chemical Formula 19 | 45.7 ± 4.0 |
| | Chemical Formula 20 | 42.6 ± 3.1 |
| Positive control | α-tocopherol | 25.4 ± 0.9 |
| | BHA | 15.3 ± 0.6 |

Example 3

Measurement of Lipid Peroxidation Inhibitory Activity

In order to measure anti-oxidant activities of the compounds represented by <Chemical Formula 1>-<Chemical Formula 20>, separated in the above Example 1, their lipid peroxidation inhibitory activities were investigated. Oxidation of lipid generates oxides such as lipid hydroperoxides, conjugated fatty acids (HODEs), epoxy fatty acids, malondialdehyde (MDA) and 4-hydroxynonenal (4-HNE), causing direct damages on biomembrane constituting a cell or secondary reaction with other cell components. Thus, oxidation of lipid is believed to be one of major reasons of degenerative diseases and aging (Esterbauer, H. et al., *Free Radic. Biol. Med.*, 1991, 11:81-128; Esterhauer, H., Cheeseman, K. H., *Methods Enzymol.*, 1990, 186:407-421; Jira, W., et al., *Chem. Phys. Lipids*, 1996, 84:165-173; Jira, W. et al., *Biosci*, 1998, 53:1061-1071). In general, superoxide radical, generated in electron transport system of a cell like mitochondria or microsome, is changed into $H_2O_2$ by an enzyme reaction in vivo, and further changed into harmless water by an enzyme such as catalase or glutathione peroxidase. But, as active oxygen is increased by any reason, $H_2O_2$ produces hydroxyl radical (HO.) by Fenton reaction ($Fe^{2+}+H_2O_2 \rightarrow Fe^{3+}+HO.+HO^-$) or metal-catalysed Haber-Weiss reaction ($O^{2-}+H_2O_2 \rightarrow O_2+HO.+HO^-$), leading to the generation of lipid peroxides. The lipid peroxides are reacted again with metallic ions in viva to induce lipid radical. (L.) or lipid peroxiradical (LOO.), resulting in lipid peroxidative chain reaction (Halliwell, B., Gutteridge, J. M. C., Free radicals in biology and medicine, 3rd Edition, Oxford University Press, Oxford, 1999; Halliwell, B., Gutteridge, J. M. C., *Biochem. J.*, 1999, 219:1-14; Harman, D., Free radical theory of aging. Alan R Liss, New York, 1986, 3-49; Stadtman, E. R., Levine, R. L., *Ann. NY Acad. Sci.*, 2000, 899:191-208). Therefore, a compound having an electron donating capability is regarded to have a lipid peroxidation inhibitory activity.

The lipid peroxidation inhibitory activity can be quantified by a spectroscopic method in which malondialdehyde, generated by lipid oxidation caused by hydroxyl radical, a final product of $Fe^{2+}$/ascorbic acid reaction system, was reacted with thiobarbituric acid (referred as 'TBA' hereinafter). Particularly, 10 µl of each compound represented by <Chemical Formula 1>-<chemical Formula 20> was mixed with 50 µl, of rat brain homogenates having the protein concentration of 10 mg/ml and 740 µl of 50 mM phosphate buffer (pH 7.4). And then, the mixture (200 µl) of 0.1 mM $FeSO_4.7H_2O_2$ and 1 mM ascorbic acid was added thereto, followed by a reaction at 37° C. for 30 minutes. 250 µl of 20% trichloroacetic acid (referred as 'TCA' hereinafter) (Sigma) was added into the reaction solution to terminate the reaction. Then, 250 µl, of 1% TBA (Sigma) was added, which was reacted at 100° C. for 10 minutes. The reaction solution was centrifuged with 10,000 rpm for 10 minutes, after which $OD_{532}$ was measured. The lipid peroxidation inhibitory activity of each sample was calculated according to the below <Mathematical Formula 2>, and IC$_{50}$ was determined by the concentration that is enough to inhibit lipid peroxidation by 50%. BHA and α-tocopherol were used for comparing groups and no sample or solution was added to a control group.

Lipid Peroxidation Inhibitory Activity (%)=($A_{control}$−$A_{sample}$)/($A_{control}$−$A_{blank}$)×100   <Mathematical Formula 2>

$A_{control}$: Optical density of control group (sample was not added), $A_{sample}$: Optical density of experimental group (sample was added), $A_{blank}$: Optical density of a group not added with sample, TCA and TBA.

As a result, compounds of flavonoids, stilbenes and phenolics showed strong lipid peroxidation inhibitory activities, dose dependently. Especially, a compound represented by <Chemical Formula 5> (piceatannol) of stilbenes was proved to have as strong activity (IC$_{50}$: 0.09±0.01 g/ml) as BHA (IC$_{50}$: 0.11±0.02 g/ml), known as a powerful lipid peroxidation inhibitor. And most of flavonoid compounds showed strong lipid peroxidation inhibitory activities. In particular, IC$_{50}$ values of compounds represented by <Chemical Formula 9> (myricetin), <Chemical Formula 17> ((−)-epicatechin-3-O-gallate), <Chemical Formula 18> ((−)-epigallocatechin-3-O-gallate), <Chemical Formula 11> (quercitrin), <Chemical Formula 12> (myricitrin) and <Chemical Formula 13> (myricetin-3-O-(2-O-galloyl)-a-L-rhamnopyranoside) were 0.95±0.06, 2.9±0.06, 1.0±0.08, 6.21±0.40, 5.27±0.32 and 4.73±0.41 g/ml, respectively, which were all superior to the lipid peroxidation inhibitory activity of α-tocopherol, used as a positive control (Table 4). Lipid peroxidation inhibitory activity, like DPPH radical scavenging activity of the above Example 2, seems to be related to the stabilization of phenoxy radical. That is, the more electron-donating groups are replaced in benzene ring, the easier phenoxy radical becomes stable, causing the increase of the activity. Especially, the structure of a flavonoid compound contributes not only to the effective stabilization of phenoxy radical but also to the chelation of a metal ion, because of which the compound has a powerful lipid peroxidation inhibitory activity.

TABLE 4

| Classification | Compound | Lipid Peroxidation Inhibitory Activity $IC_{50}$ (μg/ml) |
|---|---|---|
| Chalcones | Chemical Formula 1 | 3.33 ± 0.50 |
| | Chemical Formula 2 | 12.81 ± 1.86 |
| | Chemical Formula 3 | 6.05 ± 0.99 |
| Stilbenes | Chemical Formula 4 | 0.89 ± 0.10 |
| | Chemical Formula 5 | 0.09 ± 0.01 |
| Phenolics | Chemical Formula 6 | 6.80 ± 0.63 |
| | Chemical Formula 7 | 7.05 ± 0.87 |
| | Chemical Formula 8 | 7.01 ± 0.62 |
| Flavonols | Chemical Formula 9 | 0.95 ± 0.06 |
| | Chemical Formula 10 | 10.25 ± 0.91 |
| | Chemical Formula 11 | 6.21 ± 0.40 |
| | Chemical Formula 12 | 5.27 ± 0.32 |
| | Chemical Formula 13 | 4.73 ± 0.41 |
| | Chemical Formula 14 | 19.0 ± 1.52 |
| | Chemical Formula 15 | 10.10 ± 1.02 |
| Flavanols | Chemical Formula 16 | 4.71 ± 0.26 |
| | Chemical Formula 17 | 2.90 ± 0.06 |
| | Chemical Formula 18 | 1.00 ± 0.08 |
| Lignans | Chemical Formula 19 | 37.42 ± 2.06 |
| | Chemical Formula 20 | 39.10 ± 3.11 |
| Positive control | α-tocopherol | 6.61 ± 0.95 |
| | BHA | 0.11 ± 0.02 |

Example 4

Measurement of Hydroxyl Radical Scavenging Activity and Nitric Oxide Scavenging Activity Hydroxyl radical (HO.) is generated by the reaction of a metal ion or a superoxide radical. Owing to its strong reactivity, hydroxyl radical causes oxidative damages to DNA, protein and lipid in vivo. Nitric oxide (NO.) is reacted with a superoxide radical to generate a peroxy nitrite (ONOO—), also having strong reactivity. So, it shows similar action to hydroxyl radical in vivo (Yan, L. J., Sohal, R. S., *Free Radic. Biol. Med.*, 2000, 29:1143-1150). Thus, the present inventors measured hydroxyl radical scavenging activity according to the method of Halliwell (Halliwell, B. et al., Anal Biochem., 1987, 165, 215-219) in order to investigate anti-oxidant activities of compounds represented by <Chemical Formula 1>-<Chemical Formula 20>, separated in the above Example 1. Particularly, each compound was mixed with 10 μg of a sample dissolved in DMSO, phosphate buffer (20 mM, pH 7.4) 5.6 mM deoxyribose, 0.1 mM $FeCl_3$, 1 mM $H_2O_2$ and 0.1 mM ascorbic acid, making total volume 1 ml, which was then reacted at 37° C. for 60 minutes. 250 μl of 20% TCA and 250 μl of 1% TBA solution (dissolved in 50 mM NaOH) were added to the reaction solution, followed by thermal reaction at 95° C. for 5 minutes. After completing the reaction, $OD_{532}$ was measured. Hydroxyl radical scavenging activity was calculated by the below <Mathematical Formula 3>. BHA and α-tocopherol were used for a positive control.

Hydroxyl Radical Scavenging Activity (%)=$(A_{control}-A_{sample})/(A_{control}-A_{blank})\times 100$  <Mathematical Formula 3>

$A_{control}$: Optical density of control group well (sample was not added), $A_{sample}$: Optical density of experimental group well (sample was added), $A_{blank}$: Optical density of well not added with sample, TCA and TBA As a result, the compounds of flavonoids, stilbenes and phenolics showed 12.7-54.0% hydroxyl radical scavenging activity, comparing to a control group. Especially, the compounds represented by <Chemical Formulas 17> ((–)-epicatechin-3-O-gallate), <Chemical Formula 18> ((–)-epigallocatechin-3-O-gallate), <Chemical Formula 7> (methyl gallate), <Chemical Formula 8> (ethyl gallate) and <Chemical Formula 13> (myricetin-3-O-(2-O-galloyl)-a-L-rhamnopyranoside), in which all galloyl groups were replaced, showed remarkably higher hydroxyl radical scavenging activities (Table 5).

In the other hand, the compounds represented by <Chemical Formulas 18> ((–)-epigallocatechin-3-O-gallate), <Chemical Formula 17> ((–)-epicatechin-3-O-gallate), <Chemical Formula 16> ((+)-catechin) and <Chemical Formula 9> (myricetin) showed a comparatively high nitric oxide scavenging activity (Table 5).

TABLE 5

| Classification | Compound | Hydroxyl radical scavenging activity (%) | Nitric oxide scavenging activity (%) |
|---|---|---|---|
| Chalcones | Chemical Formula 1 | 6.1 | |
| | Chemical Formula 2 | 4.5 | |
| | Chemical Formula 3 | 3.2 | |
| Stilbenes | Chemical Formula 4 | 9.4 | 26.5 ± 1.4 |
| | Chemical Formula 5 | 12.7 | 30.8 ± 1.9 |
| Phenolics | Chemical Formula 6 | 33.6 | 25.0 ± 2.0 |
| | Chemical Formula 7 | 43.8 | 32.6 ± 2.8 |
| | Chemical Formula 8 | 44.0 | 33.4 ± 2.1 |
| Flavonols | Chemical Formula 9 | 8.7 | 25.9 ± 0.8 |
| | Chemical Formula 10 | 3.0 | 5.9 ± 0.5 |
| | Chemical Formula 11 | 16.6 | 10.2 ± 1.0 |
| | Chemical Formula 12 | 19.5 | 11.9 ± 0.9 |
| | Chemical Formula 13 | 45.4 | 23.0 ± 0.6 |
| | Chemical Formula 14 | 10.2 | 6.0 ± 0.8 |
| | Chemical Formula 15 | 16.4 | 14.1 ± 1.4 |
| Flavanols | Chemical Formula 16 | 12.7 | 16.9 ± 1.1 |
| | Chemical Formula 17 | 39.9 | 25.4 ± 1.2 |
| | Chemical Formula 18 | 54.0 | 26.2 ± 0.9 |
| Lignans | Chemical Formula 19 | 7.3 | 0.8 ± 0.6 |
| | Chemical Formula 20 | 8.1 | 0.8 ± 0.8 |
| Positive control | α-tocopherol | 0.8 | |
| | BHA | 15.6 | |

Example 5

Measurement of Superoxide Radical Scavenging Activity

Superoxide radical ($O^{2-}$) itself has a little reactivity, but is easily changed into $H_2O_2$ that generates hydroxyl radical having strong reactivity or is reacted with nitric oxide (NO.) to generate peroxy nitrite ($ONOO^-$) having strong reactivity, too. Thus, it might be a reason for oxidation of SH-group, nitration of protein tyrosine, lipid peroxidation and DNA damage. In order to measure anti-oxidant activities of the compounds represented by <Chemical Formula 1>-<Chemical Formula 20>, prepared in the above Example 1, their superoxide radical ($O^{2-}$) scavenging activities were measured, since superoxide radical works as a precursor of many harmful active oxygen. Basically, measurement of superoxide radical scavenging activity was performed by investigating the activity of superoxide dismutase (SOD), an enzyme scavenging superoxide by dismutation of the same. In the present invention, an activity of a sample to inhibit superoxide production by the enzyme reaction of xanthine/xanthine oxidase and its another activity to inhibit reaction ($NBT + 2O^{2-} \rightarrow NBTH_2 + 2O_2$) generating formazan by reduction of nitro blue tetrazolium (referred as 'NBT' hereinafter) were measured. Particularly, wells of a 96-well plate were supplemented with 50 μl of 4 mM xanthine (Sigma), 50 μl of 250 mM NBT (Sigma), 50 μl of 50 mM phosphate buffer (pH 7.8, 1 mM EDTA) and 10 μl of each sample, into which 40 μl of xanthine oxidase was added to induce a reaction. After the reaction was completed, each reaction solution was collected as scheduled, and $OD_{550}$ was measured with an ELISA reader. As shown in the below <Mathematical Formula 4>, superoxide radical scavenging activity of each sample was calculated by comparing the decrease of reduction of NBT with that of a control group, and $IC_{50}$ was determined as the concentration of a sample that is able to scavenge superoxide radical by 50%. α-tocopherol and caffeic acid were used for a positive control to compare the anti-oxidant activity with others.

Superoxide Radical Scavenging Activity (%)=
$(A_{control} - A_{sample})/(A_{control} - A_{blank}) \times 100$  <Mathematical Formula 4>

$A_{control}$: Optical density of control group well (sample was not added), $A_{sample}$: Optical density of experimental group well (sample was added), $A_{blank}$: Optical density of well not added with sample, TCA and TBA.

As a result, the compounds of flavonoids, stilbenes and phenolics showed excellent radical scavenging activities, dose dependently. Especially, $IC_{50}$ values of the flavan-3-ol compounds represented by <Chemical Formula 17> ((−)-epicatechin-3-O-gallate), <Chemical Formula 18> ((−)-epigallocatechin-3-O-gallate) and <Chemical Formula 15> (myricetin-3-O-(2-O-galloyl)-a-L-rhamnopyranoside) were 11.9±2.1, 24.0±3.5 and 13.2±2.5 g/ml, respectively, reflecting a powerful activity that was similar to that of caffeic acid, known as an effective superoxide radical scavenger (IC50 11.0±1.8 g/ml). And also, the compounds of flavonoids and phenolics showed excellent superoxide radical scavenging activities. In particular, $IC_{50}$ values of the compounds represented by <Chemical Formula 9> (myricetin), <Chemical Formula 16> ((+)-catechin), <Chemical Formula 7> (methyl gallate) and <Chemical Formula S> (ethyl gallate) were 12.1±1.1, 16.5±2.0, 16.5±1.4 and 15.8±1.6 g/ml, respectively. On the contrary, the compounds of chalcones had comparatively weak scavenging activities. Compounds having a structure that makes phenoxy radical, generated during the reaction with superoxide, stable were confirmed to have an excellent superoxide radical scavenging activity. Especially, the compounds in which galloyl group was replaced showed the strong activity (Table 6).

TABLE 6

| Classification | Compound | Superoxide radical scavenging activity IC50 (μg/ml) |
|---|---|---|
| Chalcones | Chemical Formula 1 | 47.6 ± 4.0 |
| | Chemical Formula 2 | 49.8 ± 3.1 |
| | Chemical Formula 3 | 59.2 ± 3.8 |
| Stilbenes | Chemical Formula 4 | 45.3 ± 1.9 |
| | Chemical Formula 5 | 12.1 ± 1.7 |
| Phenolics | Chemical Formula 6 | 34.1 ± 2.4 |
| | Chemical Formula 7 | 16.5 ± 1.4 |
| | Chemical Formula 8 | 15.8 ± 1.6 |
| Flavonols | Chemical Formula 9 | 12.1 ± 1.1 |
| | Chemical Formula 10 | 50.2 ± 3.4 |
| | Chemical Formula 11 | 32.1 ± 2.0 |
| | Chemical Formula 12 | 29.7 ± 1.8 |
| | Chemical Formula 13 | 13.2 ± 2.5 |
| | Chemical Formula 14 | 45.2 ± 2.2 |
| | Chemical Formula 15 | 37.1 ± 2.0 |
| Flavanols | Chemical Formula 16 | 16.5 ± 2.0 |
| | Chemical Formula 17 | 11.9 ± 2.1 |
| | Chemical Formula 18 | 24.0 ± 3.5 |
| Lignans | Chemical Formula 19 | >100 |
| | Chemical Formula 20 | >100 |
| Positive control | Caffeic acid | 11.0 ± 1.8 |
| | BHA | 48.8 ± 2.5 |

Example 6

Activity to Protect Cells from Oxidative Damages Induced by t-butylhydroperoxide t-butylhydroperoxide is metabolized into a free radical intermediate as it comes in a cell, so that it causes lipid peroxidation, resulting in cell damage. This phenomenon is similar to that caused by oxidataive stress accumulated in cells and tissues. Thus, in fact, it might be very effective to evaluate the inhibition of aging caused by oxidative stress. HEK-N/F, an epidermal cell line of a newborn baby, was treated with 1.5 mM of t-butylhydroxyperoxide for 3 hours. As a result, cell survival rate was decreased remarkably by 11.2±1.2%. But, when the compounds separated above were treated thereto additionally by the concentration of 50.0 g/ml, a strong cell-protecting activity was detected. In particular, when the compound represented by <Chemical Formula 5> (piceatannol) was treated together, cell survival rate reached 84.7±6.9%, reflecting a very strong cell-protecting activity. Besides, flavone-3-ol compounds represented by <Chemical Formula 9> (myricetin) and <Chemical Formula 11> (quercetin) showed 61.0±4.5% and 48.1±5.7% cell survival rates. And cell-protecting activities of the compounds represented by <Chemical Formula 6> (gallic acid), <Chemical Formula 7> (methyl gallate) and <Chemical Formula 8> (ethyl gallate) were 41.5±3.1%, 43.0±5.6% and 43.1±4.1%, respectively. From the results, the compounds extracted from *Cercis chinensis* of the present invention were confirmed to be able to inhibit aging caused by oxidative stress by protecting cells from oxidative stress and inhibiting cell death induced by peroxidation.

TABLE 7

| Classification | Compound | Cell survival rate (%) | TBARS (pmol/mg protein) |
|---|---|---|---|
| Chalcones | Chemical Formula 1 | 13.9 ± 12.6 | 5118.1 ± 410.5 |
| | Chemical Formula 2 | 16.2 ± 3.2 | 3449.7 ± 305.8 |
| | Chemical Formula 3 | 12.1 ± 1.0 | 8255.1 ± 576.4 |
| Stilbenes | Chemical Formula 4 | 18.1 ± 1.6 | 2792.4 ± 259.1 |
| | Chemical Formula 5 | 84.7 ± 6.9 | 520.2 ± 60.7 |
| Phenolics | Chemical Formula 6 | 41.5 ± 3.1 | 1245.7 ± 112.4 |
| | Chemical Formula 7 | 43.0 ± 5.6 | 1024.4 ± 91.9 |
| | Chemical Formula 8 | 43.1 ± 4.1 | 1115.6 ± 96.2 |
| Flavonols | Chemical Formula 9 | 61.0 ± 4.5 | 810.7 ± 77.0 |
| | Chemical Formula 10 | 16.8 ± 1.3 | 3295.1 ± 304.5 |
| | Chemical Formula 11 | 21.4 ± 1.9 | 2217.2 ± 200.3 |
| | Chemical Formula 12 | 25.4 ± 1.7 | 1852.6 ± 126.8 |
| | Chemical Formula 13 | 45.1 ± 3.6 | 1019.8 ± 154.0 |
| | Chemical Formula 14 | 20.0 ± 2.6 | 2928.1 ± 209.9 |
| | Chemical Formula 15 | | |
| Flavanols | Chemical Formula 16 | 24.5 ± 1.9 | 1912.4 ± 112.0 |
| | Chemical Formula 17 | 49.4 ± 6.4 | 1007.3 ± 95.2 |
| | Chemical Formula 18 | 46.6 ± 5.9 | 1032.6 ± 103.5 |
| Lignans | Chemical Formula 19 | 13.5 ± 2.0 | 5981.1 ± 412.6 |
| | Chemical Formula 20 | 12.9 ± 2.1 | 7635.7 ± 631.2 |
| Control group | t-butanol | 11.2 ± 1.2 | 984.0 ± 95.2 |

Example 7

Activity to Protect Cells from Oxidative Stress Caused by UV Irradiation

<7-1> Cell Protecting Effect from UV Irradiation (In Vitro)

UV irradiation induces DNA damage and DNA-protein connection by increasing active oxygen in cells. When HEK-N/F cells were irradiated by 35 mJ/cm$^2$ of UVB, DNA chains in nucleus were cut. After uniting the broken chains to ethidium homodimer (Et2), a DNA chain intercalating fluorescent dye, extent of fluorescence was measured to quantify the amount of DNA damage. Particularly, HEK-N/F cells were cultured on serum-free KGM medium (Clonetics), which were inoculated into wells of a 24-well plate by 0.5–4×10$^4$ cells/2 cm$^2$. Then, the cells were cultured for 18 hours, after which a sample was treated thereto for 2 hours. After being washed with PBS, the cells were irradiated by UV using a UV transilluminator (Spectronics UV transilluminator EBF-260, the maximal wavelength, 312 nm; a half-peak intensity range, 297-328 nm). The cells exposed on UV were further cultured for 1-7 hours, and then, 5 M ethidium homodimer (Et2, Millipore) was added. 30 minutes later, fluorescence was measured with Millipore microplate fluorometer Cytofluor 2350 (excitation: 485 nm, emission: 645 nm).

Figure 6A:
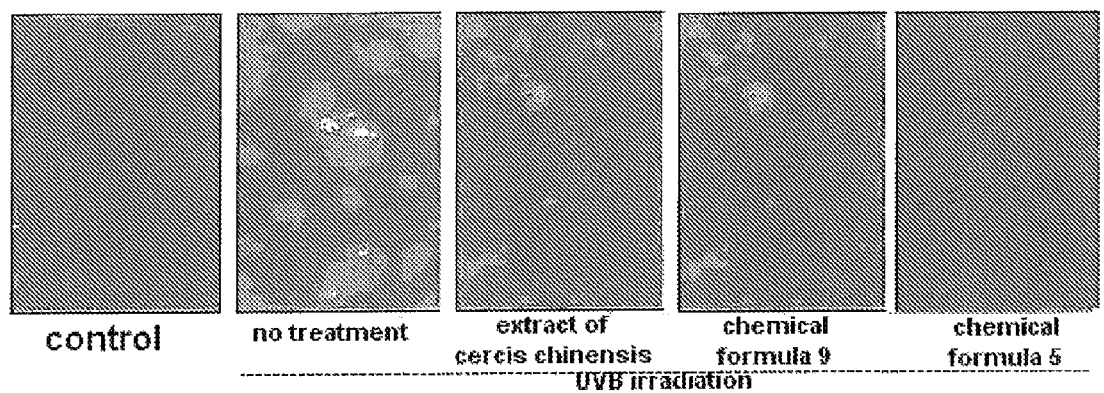
FIG. 6a is a set of photographs of a cell showing DNA damages, reflecting a cell protecting effect against UV irradiation of an extract of *Cercis chinensis* of the present invention or a compound separated from the same.
Figure 6B:
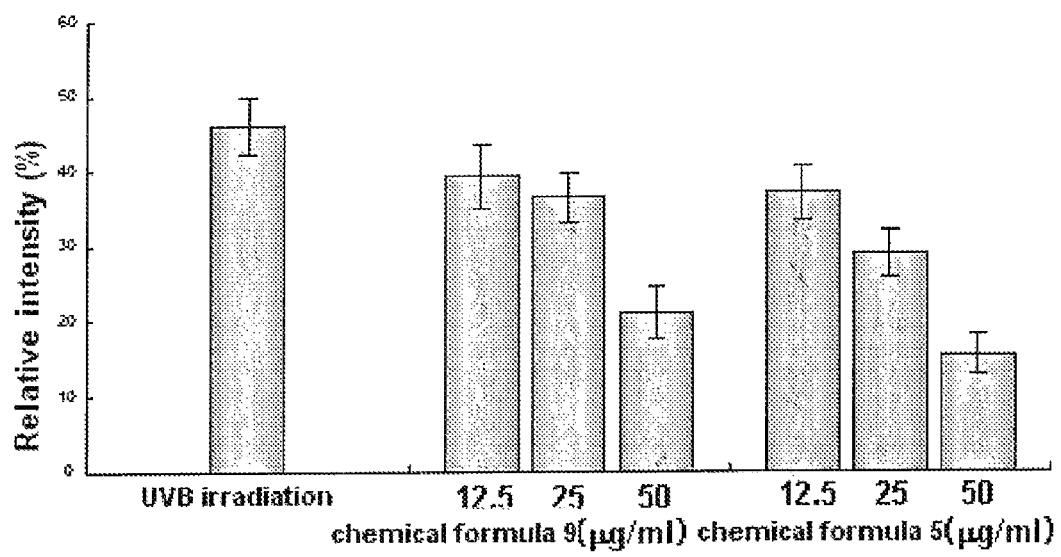
FIG. 6b is a graph showing relative intensity of fluorescence showing DNA damages, reflecting a cell protecting effect against UV irradiation of an extract of *Cercis chinensis* of the present invention and a compound separated from the same.

As a result, as shown in FIG. 6a and FIG. 6b, fluorescence, seen in groups treated with an extract of Cercis chinensis and the compounds represented by <Chemical Formula 9> (myricetin) and <Chemical Formula 5> (piceatannol), was each 54.7% and 66.7% lower than that of a control So, an extract of Cercis chinensis and active components separated from the same were confirmed to lessen DNA damages remarkably by inhibiting oxidative stress caused by UV irradiation.

<7-2> Activity to Protect Skin Tissues from UV irradiation (In Vitro)

5-6 week old female hairless mice (SKH-hr 1) were raised for 14 days at 24±2° C. with 50±10% relative humidity and 12 hour day/night cycle. 30-60 minutes before the experiment, a sample was hyperdermically injected on 5 spots of the mice and the backs of the mice were irradiated by UVB. 5 mice per each group were put in a cage (20×15×5 cm) and UVB irradiation was performed using a UV lamp (HP-15M, 280-400 nm, max. 312 nm; Atto Co., Japan) at 15 cm distance by 15 kJ/m$^2$. After the completion of UV irradiation for 24 hours, back skin was cut and stored at −70° C. until peroxidation was measured.

UVB irradiation causes serious lipid peroxidation in skin tissues, so measurement of the peroxided lipid content might lead to the measurement of skin damages. Particularly, UVB was irradiated on the back skin of SKH-1 hairless mouse. 48 hours later, the back skin tissues were cut to measure lipid peroxidation by thiobarbituric acid (TBA) method. The back skin of the mouse was put in a 10×50 mM K-P buffer solution for homogenation.

Hydrogen peroxidation was also investigated. The frozen back skin section was put in 0.1 M Tris-HCl buffer solution (pH 7.5) containing 1 mg/ml of glucose and 1 mg/ml diaminobenzidine (DAB), which was cultured at 37° C. for 5-6 hours. After being washed with distilled water, the solution was stained with 2% methyl green for 60 minutes. Nucleus stained blue and DAB peroxidase (brown) were observed under a microscope.

Figure 7:
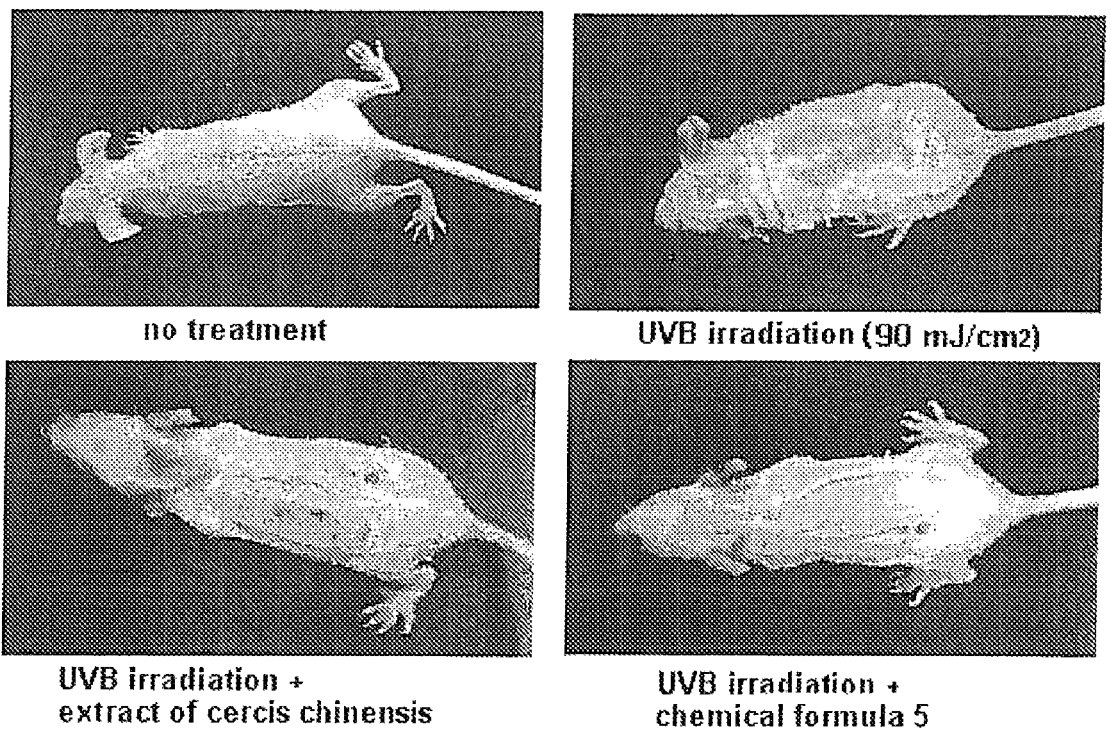
FIG. 7 is a set of photographs showing skin damages of a nude mouse, confirming a cell protecting effect against UV irradiation of an extract of *Cercis chinensis* of the present invention and a compound separated from the same.

UV irradiation induces the generation of active oxygen species in skin tissues, causing DNA damages, protein oxidation and lipid peroxidation, which were reasons of skin damages such as inflammation, cancer, aging, etc. As shown in FIG. 7, UVB irradiation with 90 mJ/cm$^2$ caused serious skin damage. But, when an extract of Cercis chinensis and a compound represented by <Chemical Formula 5> (piceatannol) were pretreated by 50 mg/kg each, a skin damage in SKH-1 hairless mouse was remarkably reduced. So, an extract of Cercis chinensis and its active ingredient, a compound represented by <Chemical formula 5> (piceatannol), must have activities to protect skin cells from oxidative stress, to inhibit lipid peroxidation and to scavenge radicals. And, the activity to protect skin from UVB irradiation seemed to be resulted from such anti-oxidant activity. Diaminobenzidine (DAB) generates dark brown DAB peroxidase by being reacted with peroxidase in tissues. So, H$_2$O$_2$ generated by UVB irradiation was observed. As shown in FIG. 7, under UVB irradiation with 90 mJ/cm$^2$, dark brown DAB-peroxidase was observed much, but H$_2$O$_2$ generation was remarkably inhibited in SKH-1 hairless mouse skin tissues as being pre-treated with an extract of Cercis chinensis and a compound represented by <Chemical Formula 5> (piceatannol) by 50 mg/kg each.

From the investigation of lipid peroxidation, it was confirmed that an average TEARS (thiobarbituric acid reactive substances) content in groups irradiated by UVB was about 0.68 nmol/mg protein, which was twice as much peroxidation as a control group (0.32±0.05 nmol/mg protein) not irradiated by UVB (Table 8). Lipid peroxidation in skin was reduced dose dependently in groups treated with an extract of *Cercis chinensis* and a compound represented by <Chemical Formula 5> (piceatannol). Especially, the compound represented by <Chemical Formula 5> showed higher activity than MAP (magnesium-L-ascorbyl-2-phosphate) used for a positive control under the equal concentration.

TABLE 8

| Treating group | Treating amount (mg/kg) | TBARS (nmol/mg protein) |
| --- | --- | --- |
| Control group | 0 | 0.32 ± 0.05 |
| UVB irradiation | 0 | 0.68 ± 0.1 |
| *Cercis chinensis* extract + UVB irradiation | 50 | 0.21 ± 0.10 |
|  | 30 | 0.34 ± 0.09 |
|  | 10 | 0.64 ± 0.10 |
| Chemical Formula 5 + UVB irradiation | 30 | 0.07 ± 0.03 |
|  | 10 | 0.16 ± 0.08 |
| MAP + UVB irradiation | 50 | 0.16 ± 0.05 |
|  | 30 | 0.28 ± 0.06 |

Example 8

Prolongation of Life Span of a Cell

HEK-N/F cells were obtained from foreskin of a newborn baby after its fibroblasts, another major component of skin, were treated with uridine bromide. Then, the cells were cultured in DMEM medium supplemented with 10 FBS. HEK-N/F cells were diluted consecutively at the ratio of 1:4 during the culture. Before being treated with samples, the cells were grown up to 3 PDL (population doubling level). During the culture, each sample was administered by 3 g/ml. Medium was replaced every three days by fresh medium supplemented with a culture solution containing the equal concentration of the sample. After culturing, an extract of *Cercis chinensis* of the present invention, a compound represented by <Chemical Formula 5> (piceatannol) and a compound represented by <Chemical Formula 9> (myricetin) were treated, followed by investigation of the cell division.

Figure 8:
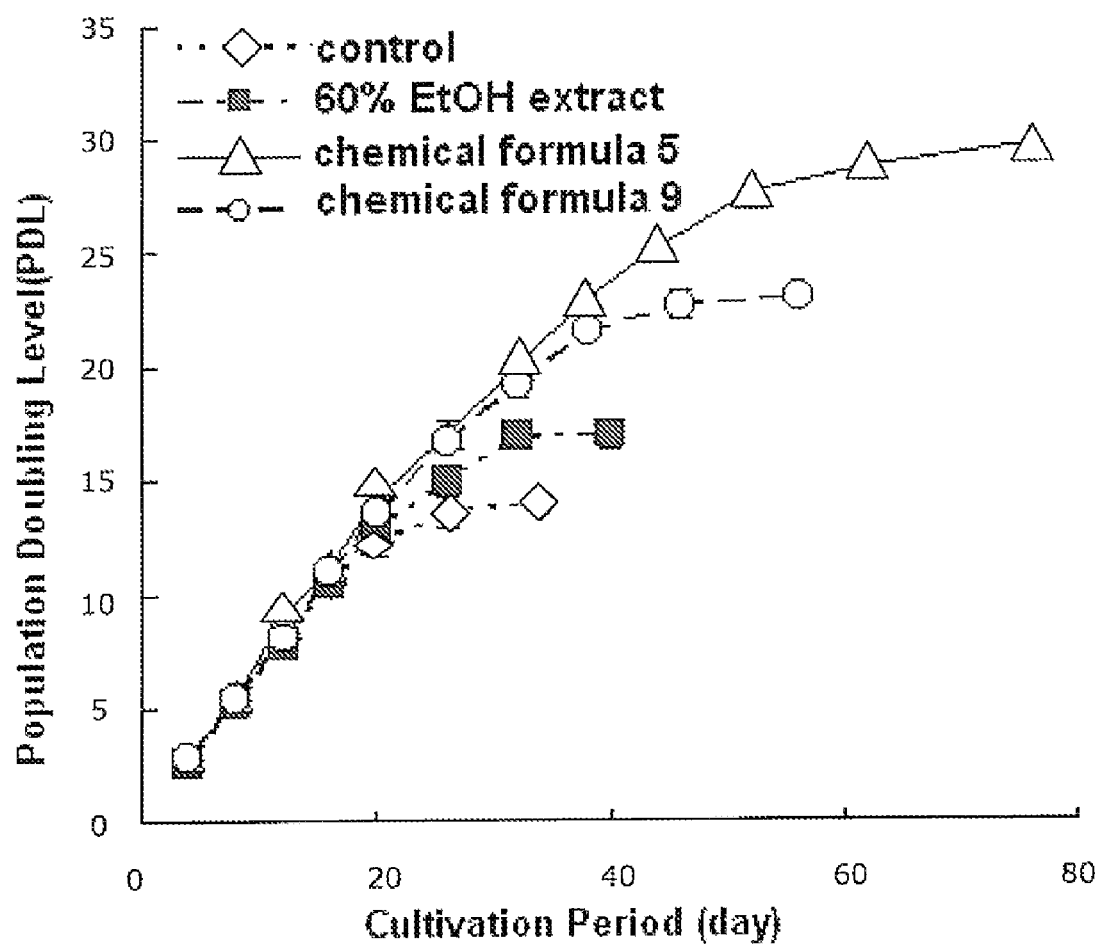
FIG. 8 is a graph showing the prolongation of life span of a cell by an extract of *Cercis chinensis* of the present invention and a compound separated from the same.

As a result, an extract of *Cercis chinensis* and its active ingredients were all confirmed to have an effect of prolonging life span of a cell. While an average life span of a cell of a control treated with nothing was about 35 days, an average life span of the group treated with an extract of *Cercis chinensis* by 3 μg/ml was about 42 days, which was 1.2 times as long as that of a control. And also, average life spans of groups treated with other active ingredients, a compound represented by <Chemical Formula 9> (Myricetin) and a compound represented by <Chemical Formula 5> (piceatannol), for culture were 56 days and 76 days respectively, which were 1.6 times and 2.1 times each as long as that of a control (FIG. 8). Thus, an extract of *Cercis chinensis* and active ingredients separated from the same were confirmed to have an effect of prolongation of life span of a cell.

Example 9

Prolongation of Life Span of a Cell and Extension of a Telomere

In the above Example 8, an extract of *Cercis chinensis* and active ingredients separated from the same were confirmed to have an effect of prolongation of life span of a cell. Thus, in this example, relation between the effect of prolongation of life span and the length of a telomere was investigated. Particularly, genomic DNA was extracted from each cell of different ages by using a nucleic acid extraction kit (Isoquick Nucleic Acid Extraction kit, ORCA Research Inc.), which was stored at 4° C. after being dissolved in Tris-EDTA solution (10 mM Tris-HCl, 1 mM EDTA, pH 8.0). 2 μl of 10×H buffer solution (TaKaRa), 2 μl of the extracted genomic DNA solution and distilled water were all mixed in a 1.5 ml tube, making final volume 19 μl. Then, 1 μl at of restriction enzyme Hinf I (6 U/l, TaKaRa) was added thereto. The mixture was reacted at 37° C. for 3-4 hours, followed by electrophoresis. For the electrophoresis, agarose (type I, Sigma) gel concentration was adjusted to 1% for bridge region and to 0.8% for bed region to prepare gel plate (Marisol KS-8405, 20×14 cm), and 1× Boyer's buffer solution (50 mM Tris-HCl, 20 mM sodium acetate, 2 mM EDTA, 18 mM NaCl, pH 8.0) was used. As a marker, 1 Kb DNA ladder was loaded by 0.5 μg. 3 μl of loading buffer was added to all of the sample, followed by electrophoresis with 35 V/cm for 20 hours. After the electrophoresis was completed, the gel was stained with ethidium bromide (2 μg/ml) for 15 minutes, which was confirmed by UV. Then, the gel was immersed in 0.25 N HCl, followed by shaking for 15 minutes. The gel was washed twice with distilled water. This gel was dipped into denaturing solution (0.2 N NaOH, 0.6 M NaCl), followed by shaking for 25 minutes at room temperature. And then, the gel was washed three times with distilled water. On a blotting device filled with 6×SSC, nitrocellulose membrane (Optitran BA-S 85, Schleicher & Schuel), 3 mm filter paper, paper towel, glass plate and weight (2 kg) were loaded in that order, followed by blotting overnight. After the blotting was finished, membrane filter was soaked in 3×SSC, and then water was discarded smoothly. The positions of the wells on the membrane were marked. The membrane was placed between filter papers, followed by baking at 80° C. for overnight. Then, prehybridization was performed at 65° C. with denatured salmon sperm DNA (Wako), after which hybridization was carried out at 50° C. by hybridization buffer (1× Denhan solution, 1 M NaCl, 50 mM Tris-HCl, 10 mM EDTA, 0.1% SDS, 50 g/ml denatured salmon sperm DNA) and 5-end [$^{32}$P]-labeled (TTAGGG)$_4$. The hybridized membrane was immersed in a washing solution (4×SSC/0.1% SDS), followed by shaking at 55° C. for 15 minutes. After being dried, the membrane was covered with wrap and set in a cassette on which X-ray film (Scientific Imaging Film, Kodak) and intensifying screen were attached. Autoradiography was performed at −80° C. for overnight. Based on the developed film and the location of the membrane, the positions of the wells were marked by a magic pen. The density peak of TRFs was detected by a laser densitometer (UltroScan XL, Pharmacia) and its mobility was calculated.

Figure 9:
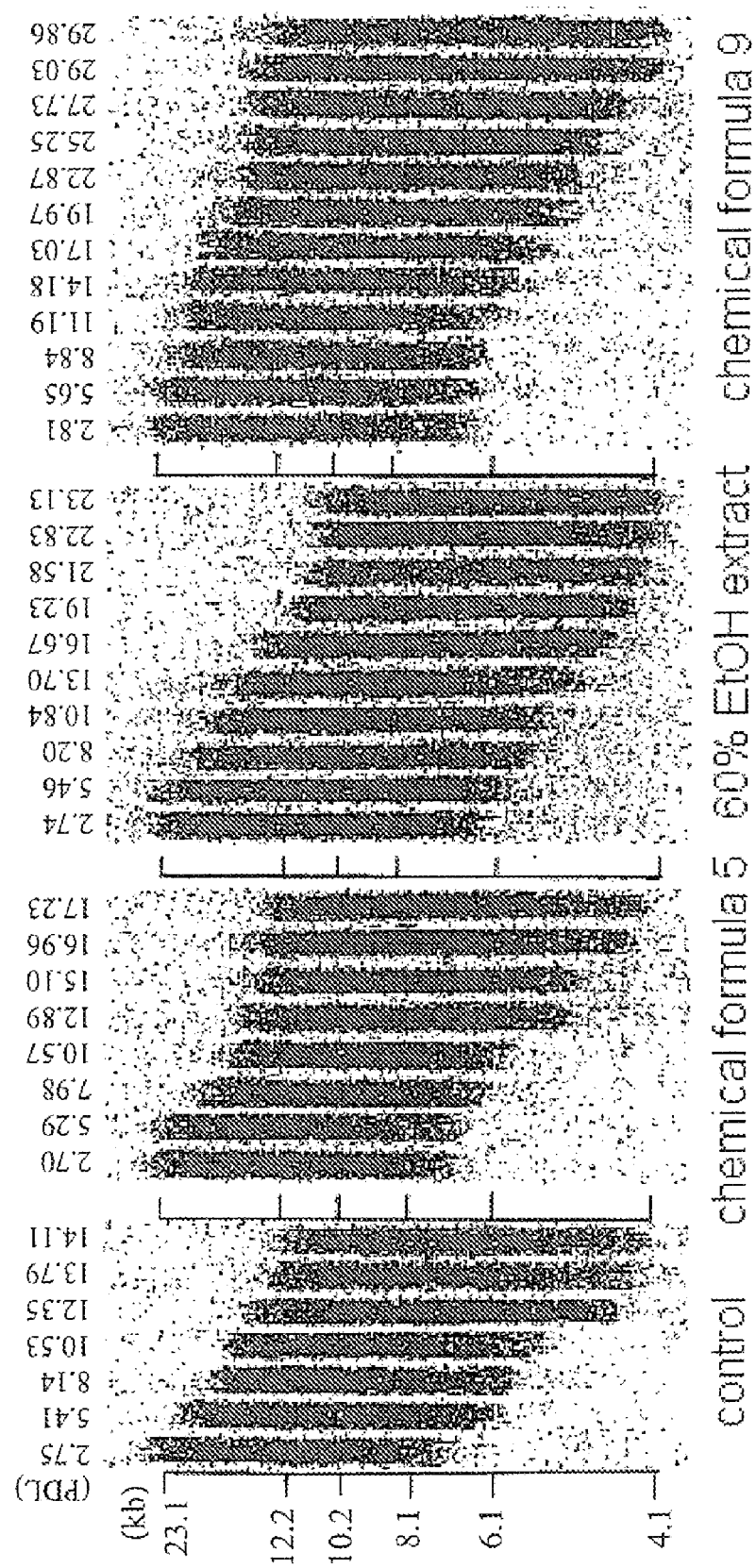
FIG. 9 is a set of photographs resulted from southern blot analysis, confirming that an extract of *Cercis chinensis* of the present invention and a compound separated from the same slow down the shortening speed of a telomere.

As a result, a telomere became shorter gradually as cell division progressed. As shown in FIG. 9, a telomere in a control group was shorter by 8.0 kbp after 14.8$^{th}$ division, and no more division was followed from then on. On the contrary, the length of a telomere in groups treated with an extract of *Cercis chinensis* or active ingredients separated from the same reached critical point (about 8.0 kbp in the present invention) after division was repeated a lot more than in a control. Cell division was continued as long as the length of a telomeric DNA was shorter over critical point (presumed to be 7.9-8.4 kb for human skin Keratinocytes). Therefore, it was confirmed that cell cycle could be extended by delaying the speed of shortening of a telomere that meant the delay of reaching critical point. While the maximum PDL of a control group was 14.1, the maximum PDLs of groups treated with an extract of *Cercis chinensis*, a compound represented by <Chemical Formula 9> (myricetin) and a compound represented by <Chemical Formula 5> (piceatannol) were 17.2, 23.1 and 29.9, respectively, suggesting the remarkable extension of the maximum PDL.

Figure 10:
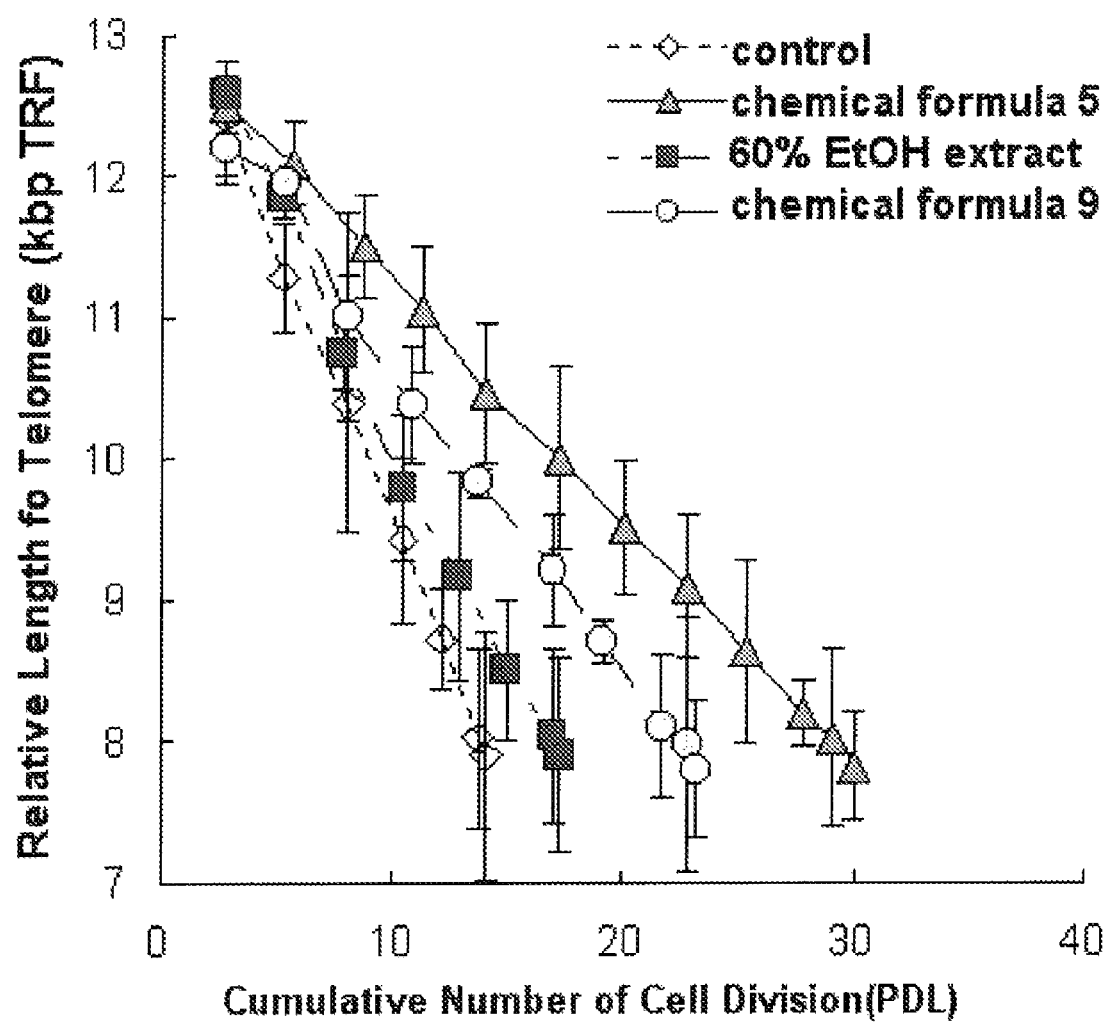
FIG. 10 is a graph showing the shortening speed of a telomere, suggesting that an extract of *Cercis chinensis* of the present invention and a compound separated from the same do prolong the length of a telomere.
Figure 11:
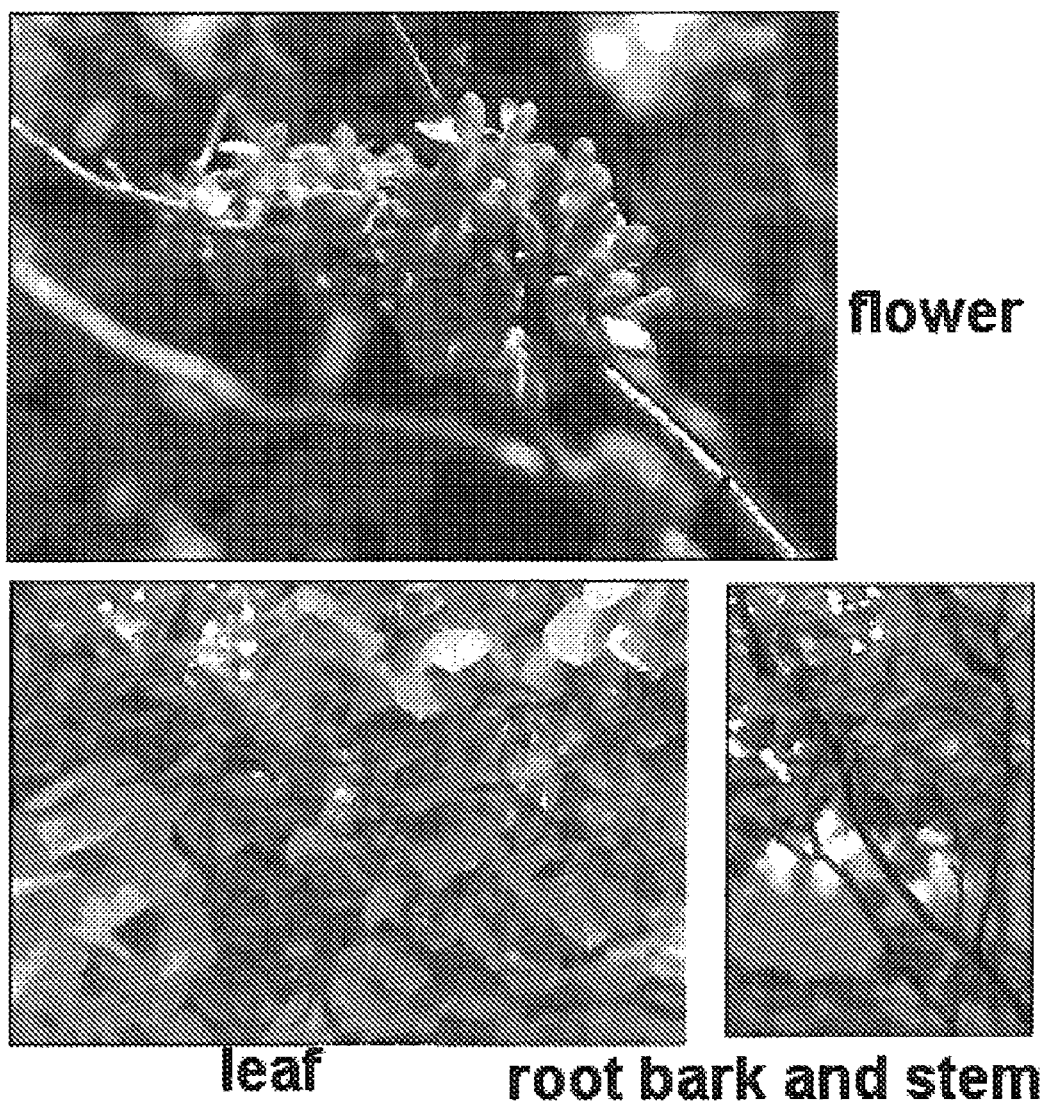
FIG. 11 is a set of photographs showing flowers, leaves, root bark and stems of *Cercis chinensis*.

Based on the relation between the frequency of cell division and the length of a telomere, telomere shortening speed was calculated. As a result, the speed of groups treated with an extract of *Cercis chinensis*, a compound represented by <Chemical Formula 9> (myricetin) and a compound <Chemical Formula 5> (piceatannol) was each 1.2 times, 1.6 times and 2.1 times delayed, comparing to that of a control (FIG. 10). Thus, the effect on prolongation of life span of a skin cell of an extract of *Cercis chinensis* and its active ingredients was confirmed to be resulted from delaying telomere-shortening speed.

Preparative Example 1

Preparation of a Cosmetic Composition Containing an Extract of *Cercis chinensis*

The present inventors prepared a cosmetic composition containing an extract of *Cercis chinensis* as an effective ingredient (preparation 1-preparation 6) as following Table 9 and Table 11. In addition to the extract of *Cercis chinensis*, other extracts, which have been generally used for making cosmetics, can be additionally included. Morus bark, brown algae, angelica root, *coix*, moutan, purslane (*Portulaca oleracea* Linne), persimmon leaves, witch hazel extract and centella extract are the examples.

At first, the present inventors prepared a soft lotion and a viscous solution containing an extract of *Cercis chinensis* of the present invention based on the below constitutions listed in Table 9 by following a general method.

TABLE 9

Preparation of a soft lotion and a viscous solution

| Raw-material (Weight %) | Preparation 1 | Preparation 2 |
| --- | --- | --- |
| 1,3-butylene glycol | 3.7 | 3.7 |
| Glycerin | 3.6 | 5.5 |
| PEG-60 hydro-generated caster oil | 0.3 | 0.1 |
| D-panthenol | 0.3 | 0.5 |
| Allantoin | 0.1 | 0.1 |
| Plant extract | 5.6 | 5.9 |
| Ethanol | 4.0 | 3.0 |
| Carbomer | 0.1 | — |
| Xanthan gum | — | 0.5 |
| Disodium EDTA | Small quantity | Small quantity |
| Dipotassium glycyrrhizate | — | Small quantity |
| Sodium hyaluronate | Small quantity | Small quantity |
| Triethanolamine | Proper quantity | Proper quantity |
| Antiseptic | Proper quantity | Proper quantity |
| Combination aromatics | Proper quantity | Proper quantity |
| *Cercis chinensis* extract | 2.0 | 4.0 |
| Purified water | to 100 | to 100 |

And next, the present inventors prepared a milky lotion and a lotion containing an extract of *Cercis chinensis* based on the constitutions listed in the below Table 10 by following a general method.

TABLE 10

Preparation of a milky lotion and a lotion

| Raw-material (weight %) | Preparation 3 | Preparation 4 |
| --- | --- | --- |
| 1,3-butylene glycol | 6.5 | 4.5 |
| Glycerin | 1.2 | 3.0 |
| D-panthenol | 0.2 | 0.1 |
| Xanthan gum | — | 0.5 |
| Plant extract | 6.2 | 6.3 |
| Magnesium aluminum silicate | — | 0.3 |
| Ethanol | 3.0 | — |
| PEG-60 hydro-generated caster oil | — | 0.2 |
| Carbomer | 0.1 | 0.1 |
| Stearic acid | 1.5 | — |
| Polysorbate 60 | 0.7 | 0.2 |
| Lipophilic glycerylstearate | 0.6 | — |
| Sorbitancesquinoliate | 0.3 | — |
| Setearylalcohol | 0.6 | — |
| Mineral oil | 5.0 | — |
| Squalane | 3.5 | 1.0 |
| Carlyric/capric triglyceride | 3.0 | 0.7 |
| Vegetable oil | 2.0 | 2.3 |
| Dimethicone | 0.4 | Proper quantity |
| Dipotassium glycyrrhizate | Small quantity | Small quantity |
| Allantoin | Small quantity | Small quantity |
| Sodium hyaluronate | Small quantity | Small quantity |
| Tocopheryl acetate | Proper quantity | Proper quantity |
| Triethanolamine | Proper quantity | Proper quantity |
| Antiseptic | Proper quantity | Proper quantity |
| Combination aromatics | Proper quantity | Proper quantity |
| *Cercis chinensis* extract | 5.0 | 6.0 |
| Purified water | to 100 | to 100 |

And next, the present inventors prepared a cream containing an extract of *Cercis chinensis* based on the constitutions listed in the below Table 11 by following a general method.

TABLE 11

Preparation of a cream

| Raw-material (weight %) | Preparation 5 | Preparation 6 |
|---|---|---|
| 1,3-butylene glycol | 7.0 | 5.0 |
| Glycerine | 1.0 | 5.0 |
| D-panthenol | 0.1 | 0.1 |
| Plant extract | 3.2 | 2.7 |
| Magnesium aluminum silicate | 0.3 | — |
| PEG-40 stearate | 1.2 | 0.8 |
| Stearic acid | 2.0 | 3.2 |
| Polysorbate 60 | 1.5 | 0.9 |
| Lipophilic glycerylstearate | 2.0 | 2.0 |
| Sorbitancesquinoliate | 1.5 | 1.0 |
| Setearylalcohol | 3.0 | 2.9 |
| Microcrystalline wax | — | 1.0 |
| Mineral oil | 4.0 | 2.0 |
| Petrolatum | — | 0.5 |
| Squalane | 3.8 | 4.5 |
| Carlyric/capric triglyceride | 2.8 | 2.5 |
| Vegetable oil | 1.8 | 2.3 |
| Dimethicone | 0.4 | 0.4 |
| Dipotassium glycyrrhizate | Small quantity | Small quantity |
| Allantoin | Small quantity | Small quantity |
| Sodium hyaluronate | Small quantity | Small quantity |
| Pyridoxinedipalmitate | — | Small quantity |
| Xanthan gum | Proper quantity | — |
| Carbomer | — | Proper quantity |
| Tocopheryl acetate | Proper quantity | Proper quantity |
| Triethanolamine | Proper quantity | Proper quantity |
| Antiseptic | Proper quantity | Proper quantity |
| Combination aromatics | Proper quantity | Proper quantity |
| Cercis chinensis extract | 5.0 | 3.0 |
| Purified water | to 100 | to 100 |

Preparative Example 2

Preparation of a Pharmaceutical Composition Having an Anti-Oxidant Activity and an Anti-Aging Activity The present inventors prepared a pharmaceutical composition having anti-oxidant and anti-aging activities containing an extract of *Cercis chinensis* as an effective ingredient <2-1> Preparation of Syrups Syrups that contained an extract of *Cercis chinensis* of the present invention by 2% (weight/volume) as an effective ingredient were prepared as follows.

The extract of *Cercis chinensis*, saccharine and sugar were dissolved in 80 g of warm water. The solution was then cooled down. Glycerin, saccharine, flavoring agent, ethanol, sorbic acid and distilled water were mixed together to make a solution, which was added to the above cooled solution. Water was added to the mixture to make total volume 100 ml (Table 12).

TABLE 12

| Raw-material | Amount (g) |
|---|---|
| *Cercis chinensis* extract | 2 |
| Saccharine | 0.8 |
| Sugar | 25.4 |
| Glycerin | 8.0 |
| Flavoring agent | 0.04 |
| Ethanol | 4.0 |
| Sorbic acid | 0.4 |
| Distilled water | Proper quantity |

<2-2> Preparation of Tablets

Tablets each containing 15 mg of the extract as an effective ingredient were prepared as follows.

250 g of an extract of *Cercis chinensis* was mixed with 175.9 g of lactose, 180 g of potato-starch and 32 g of colloidal silicic acid. 10' gelatin solution was added to the mixture, which was pulverized enough to pass through a 14-mesh sieve. The pulverized mixture was dried, to which 160 g of potato-starch, 50 g of talc and 5 g of magnesium stearate were added to produce tablets (Table 13).

TABLE 13

| Raw-material | Amount (g) |
|---|---|
| *Cercis chinensis* extract | 250 |
| Lactose | 175.9 |
| Potato-starch | 180 |
| Colloidal silicic acid | 32 |
| Gelatin solution | 10% |
| Potato-starch | 160 |
| Talc | 50 |
| Magnesium stearate | 5 |

As explained hereinbefore, owing to a strong anti-oxidant activity of the extract of *Cercis chinensis* of the present invention, a pharmaceutical composition containing the same as an effective ingredient can be used for preventing and treating peroxidation related diseases.

Hereinafter, specific diseases, to which a pharmaceutical composition containing an extract of *Cercis chinensis* of the present invention can be applied, were explained.

However, it will be appreciated that those skilled in the art, on consideration of this disclosure, may make modifications and improvements within the spirit and scope of the present invention.

Applicable Example 1

Cancer

Cancer is developed by lots of reasons, but the most primary reason is believed to be active oxygen. That is, active oxygen destroys cells and does not allow for damaged cells to be recovered, resulting in malfunction of a cell, by which cancer is developed (Ames, B. N., *Science*, 1983, 221, 1256-1264). By the way, phenolic acid included in fruits is good for liver cancer (Sun J et al., *J Agric Food Chem*, 2002, 4; 50(25), 7449-7454), lycopene contained in a tomato works for breast cancer (Hadley C W et al., *Exp Biol Med*, 2002, 227(10), 869-80) and isoverbascoside has a positive effect on stomach cancer (Chen R C et al., *Acta Pharmacol Sin*, 2002, 23 (11), 997-1001), and such anti-oxidant agents are believed to be effective for other cancers as well. Thus, an anti-oxidant agent can be effectively used for the prevention and the treatment of various cancers, and the pharmaceutical composition of the invention having an excellent anti-oxidant activity can also be effectively used for the prevention and the treatment of cancers.

Applicable Example 2

Aging

Active oxygen, generated during the normal metabolism, destroys cell components such as lipid, protein and sugar or DNA randomly and irreversibly, so that cells get oxidative damages. The long-term accumulation of such damages causes aging and even death (Harman, A, *Free radical theory of aging*, 1986, 3-49). On the other hand, the prolongation of life span by reducing the consumption of oxygen, meaning reducing basal metabolic rate, was investigated by various methods having different conditions, for example, restricted diet, limitation in movement, etc. (Medvedev, Z. A., *Biol Rev.,* 1990, 65, 375-398; Loe, J. et al., *J. Biol. Chem.,* 1971, 32, 103-121; Sohal, R. S., *Aging,* 1982, 5, 21-24). That is, the elimination of active oxygen is one way to delay aging, so thus anti-oxidant agents eliminating active oxygen have been developed so far. Therefore, the pharmaceutical composition of the present invention having an excellent anti-oxidant activity is available for delaying aging.

Applicable Example 3

Coronary Heart Disease, Hypercholesterolemia and Arteriosclerosis

When cholesterol synthase inhibitor was treated to patients with coronary heart disease and with hypercholesterolemia, cholesterol content in low density lipid decreased, but low density lipoprotein was still protected since ubiquinone Q10 synthesis was inhibited, suggesting the agent was not so much effective for preventing peroxidation by active oxygen and thus for treating the diseases above, either. On the contrary, when anti-oxidant agents such as cerivastatin or probucol were administered to those patients, low-density lipoproteins in them were rapidly decreased (Lankin V Z et al., *Bull Exp Biol Med,* 2002, 134(1), 39-42) In another clinical test, dehydropyridine calcium antagonist lacidipine, also an anti-oxidant agent, was administered to a patient with artherosclerosis. As a result, blood pressure was lowered, cholesterol in vessel wall was reduced and the size of lesion of artherosclerosis was decreased (Haller H et al., *Drugs R D,* 2002, 3(5), 311-23). So, an anti-oxidant substance was proved to be very effective for preventing and treating cholesterol related vascular diseases such as coronary heart disease, hypercholesterolemia and arteriosclerosis. Thus, the pharmaceutical composition of the present invention having an excellent anti-oxidant activity can be effectively used for the prevention and the treatment of vascular system diseases such as coronary heart disease, hypercholesterolemia and arteriosclerosis.

Applicable Example 4

Multiple Sclerosis and Autoimmune Encephalomyelitis

ALA (alpha lipoic acid), a kind of an anti-oxidant agent, was administered to model mice with multiple sclerosis and autoimmune encephalomyelitis, in which the diseases became less serious after the administration. It suggested that oxidative stress was a major reason for multiple sclerosis and autoimmune encephalomyelitis, so that an anti-oxidant agent could be effectively used for the treatment of the said nervous related diseases (Marracci G H et al. *J Neuroimmunol,* 2002, 131 (1-2), 104-14). Therefore, the pharmaceutical composition of the present invention having an anti-oxidant activity is very useful for the prevention and the treatment of nervous related diseases such as multiple sclerosis and autoimmune encephalomyelitis.

Applicable Example 5

Cerebral Apoplexy and Alzheimer's Disease

Oxidative stress caused by active oxygen oxidizes cell components, resulting in malfunction of those cells. Such abnormal function causes functional disorders in nerve cells, accompanying stroke, trauma, etc. If such oxidative stress is accumulated for a long time without being properly treated, serious brain diseases such as cerebral apoplexy, Alzheimer's disease, etc., are developed. The brain diseases such as cerebral apoplexy and Alzheimer's disease can be effectively treated by using an anti-oxidant agent which is able to eliminate active oxygen (Perry G et al., *Comp Biochem Physiol C Toxicol Pharmacol,* 2002, 133(4), 507-13; Cecchi C et al., *Free Radic Biol Med,* 2002, 15:33(10), 1372-9; Smith M A et al., *Free Radic Biol Med,* 2002, 1:33(9), 1194-9). Therefore, the pharmaceutical composition of the present invention having an excellent anti-oxidant activity is very useful for the prevention and the treatment of brain diseases such as cerebral apoplexy, Alzheimer's disease, etc.

Applicable Example 6

Enteritis

Excessive peroxidative by-products are accumulated in leucocytes of a patient with enteritis. Cell damages caused by the accumulated peroxidative by-products in patients with enteritis work as primary and further secondary pathological mechanisms of infection of intestines. That is, oxidative stress induces inflammation in intestines, developing inflammatory enteritis (Kruidenier L et al., *Aliment Pharmacol Ther,* 2002, 16(12), 1997-2015). Therefore, the pharmaceutical composition of the present invention having an excellent anti-oxidant activity can be effectively used for the prevention and the treatment of inflammation related diseases such as inflammatory enteritis, etc.

INDUSTRIAL APPLICABILITY

As explained hereinbefore, unlike other synthetic anti-oxidant agents, the extract of *Cercis chinensis* of the present invention and the compounds separated from the same, represented by <Chemical formula 1> to <Chemical Formula 20>, do not harm to human and have an excellent anti-oxidant activity compared with other natural anti-oxidants, so that they can effectively inhibit oxidative stress in cells and prevent shortening of a telomere involved in aging of cells, resulting in the extension of life span of a cell. Therefore, the cosmetic composition of the present invention containing the extract or the compounds above as an effective ingredient can be very useful for the development of cosmetics for anti-skin aging, supporting skin elasticity and wrinkle care.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for improving wrinkles on human skin and, protecting human skin elasticity comprising:
    contacting human skin with a therapeutically effective amount of an extract of *Cercis chinensis*,
    wherein the extract of *Cercis chinensis* is prepared by extracting leaves and stem of *Cercis chinensis* with water or alcohol aqueous solution, followed by extracting with hexane, ethyl acetate, and butanol, respectively in that order.

2. The method as set forth in claim 1, wherein the alcohol aqueous solution is selected from the group consisting of methanol aqueous solution, ethanol aqueous solution, propanol aqueous solution and butanol aqueous solution.

3. The method as set forth in claim 1, wherein the alcohol aqueous solution is 50~80% ethanol aqueous solution.

4. The method as set forth in claim 1, wherein the alcohol aqueous solution is 60% ethanol aqueous solution.

5. The method as set forth in claim 1, wherein the extract contains a compound selected from the group consisting of isoliquiritigenin, 2',4'-dihydroxy-4-methoxychalcone, liquiritigenin, resveratrol, piceatannol, gallic acid, methyl gallate, ethyl gallate, myricetin, afzelin, quercitrin, myricitrin, myricetin-3-O-(2"-O-galloyl)-α-L-rhamnopyranoside, syringetin-3-O-rutinoside, syringetin-3-O-2"-O-galloyl)-rutinoside, (+)-catechin, (−)-epicatechin-3-O-gallate, (−)-epigallocatechin-3-O-gallate, (−)-lyoniresinol 3a-O-β-D-xylopyranoside and (+) -lyoniresiol 3a-O-β-D-glucopyranoside.

6. The method as set forth in claim 5, wherein the extract contains 0.01-1.00 weight % of gallic acid of the total weight of the extract, 0.01-1.00 weight % of myricitrin of the total weight of the extract, 0.01-0.5 weight % of piceatannol of the total weight of the extract.

7. The method as set forth in claim 1, wherein the extract of *Cercis chinensis* is prepared by a method comprising the steps of:
    (a) extracting *Cercis chinensis* with water or alcohol aqueous solution as an extractant to produce a crude extract;
    (b) suspending the crude extract of step (a) in distilled water to produce a suspension;
    (c) extracting the suspension of step (b) with hexane to produce a hexane fraction and a remaining suspension;
    (d) extracting the remaining suspension of step (c) with ethyl acetate to produce the ethyl acetate fraction and a remaining suspension; and
    (e) extracting the remaining suspension of step (d) with butanol to produce the butanol fraction.

8. The method as set forth in claim 7, wherein the extract contains a compound selected from the group consisting of isoliquiritigenin, 2',4'-dihydroxy-4-methoxychalcone, liquiritigenin, resveratrol, piceatannol, gallic acid, methyl gallate, ethyl gallate, myricetin, afzelin, quercitrin, myricitrin, myricetin-3-O-(2"-O-galloyl)-α-L-rhamnopyranoside, syringetin-3-O-rutinoside, syringetin-3-O-2"-O-galloyl)-rutinoside, (+)-catechin, (−)-epicatechin-3-O-gallate), (−)-epigallocatechin-3-O-gallate, (−)-lyoniresinol 3a-O-β-D-xylopyranoside and (+)-lyoniresiol 3a-O-β-D-glucopyranoside.

9. The method of claim 1, wherein the human skin is contacted with the extract of *Cercis chinensis* in a cosmetic carrier.

* * * * *